US010173211B2

(12) United States Patent
Ji et al.

(10) Patent No.: US 10,173,211 B2
(45) Date of Patent: Jan. 8, 2019

(54) ORGANIC-FREE SYNTHESIS OF SMALL PORE ZEOLITE CATALYSTS

(71) Applicant: CALIFORNIA INSTITUTE OF TECHNOLOGY, Pasadena, CA (US)

(72) Inventors: Yuewei Ji, Pasadena, CA (US); Mark A. Deimund, Pasadena, CA (US); Yashodhan Bhawe, Jurong Island (SG); Mark E. Davis, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 331 days.

(21) Appl. No.: 14/882,587

(22) Filed: Oct. 14, 2015

(65) Prior Publication Data
US 2016/0101415 A1   Apr. 14, 2016

Related U.S. Application Data

(60) Provisional application No. 62/063,593, filed on Oct. 14, 2014.

(51) Int. Cl.
B01J 29/06   (2006.01)
B01J 37/10   (2006.01)
C07C 1/20    (2006.01)
C01B 39/02   (2006.01)
B01J 29/70   (2006.01)
B01J 29/08   (2006.01)
B01J 35/10   (2006.01)

(52) U.S. Cl.
CPC ............ B01J 37/10 (2013.01); B01J 29/084 (2013.01); B01J 29/70 (2013.01); B01J 29/7015 (2013.01); B01J 35/109 (2013.01); C01B 39/026 (2013.01); C07C 1/20 (2013.01); B01J 2229/36 (2013.01); B01J 2229/37 (2013.01); B01J 2229/40 (2013.01); C07C 2529/70 (2013.01); Y02P 20/52 (2015.11); Y02P 30/42 (2015.11)

(58) Field of Classification Search
CPC ...... B01J 29/7015; B01J 29/084; B01J 29/70; B01J 2229/16; B01J 2229/36; B01J 2229/37; B01J 2229/40; B01J 35/109; B01J 37/10; C07C 2529/70
USPC ................................................... 502/60, 85
See application file for complete search history.

(56) References Cited

U.S. PATENT DOCUMENTS

| | | |
|---|---|---|
| 3,140,249 A | 7/1964 | Plank et al. |
| 3,140,251 A | 7/1964 | Plank et al. |
| 3,140,253 A | 7/1964 | Plank et al. |
| 3,904,738 A | 9/1975 | Robson |
| 4,503,024 A | 3/1985 | Bourgogne et al. |
| 4,544,538 A | 10/1985 | Zones |
| 5,026,532 A | 6/1991 | Gaffney et al. |
| 6,709,644 B2 | 3/2004 | Zones et al. |
| 7,601,662 B2 | 10/2009 | Bull et al. |
| 7,754,187 B2* | 7/2010 | Cao .................. B01J 29/80 423/703 |
| 2003/0176751 A1 | 9/2003 | Strohmaier et al. |
| 2007/0087934 A1* | 4/2007 | R.M. Martens ........ B01J 29/06 502/214 |
| 2012/0258852 A1* | 10/2012 | Martinez ............... B01J 29/041 502/60 |
| 2012/0269719 A1 | 10/2012 | Moden et al. |
| 2015/0182953 A1* | 7/2015 | Senderov ............... B01J 29/83 423/714 |

FOREIGN PATENT DOCUMENTS

WO   WO 1999/008961 A1   2/1999

OTHER PUBLICATIONS

Nedyalkova et al., "Interzeolite Conversion of FAU Type Zeolite into CHA and its Application in Nh3-SCR", Top Catal (2013), 56:550-557.*
Itakura et al., "Synthesis of high-silica CHA type zeolite by interzeolite conversion of FAU type zeolite in the presence of seed crystals", Microporous and Mesoporous Materials, 144 (2011) 91-96.*
Bleken, et al., "The Effect of Acid Strength on the Conversion of Methanol to Olefins Over Acidic Microporous Catalysts with the CHA Topology", Top. Catal. Jan. 2009, vol. 52, 218-228.
Cartlidge, et al. "Hydrothermally Stable Chabazites for the Selective Preparation of Olefins from Methanol", In Zeolites: Facts, Figures, Future, Jacobs, Eds. Elsevier: Amsterdam, 1989, 1151-1161.
Davis, et al., "Zeolite and Molecular Sieve Synthesis", Chem. Mater., 1992, vol. vol. 4, 756-768.
Froment, et al., In Catalysis in the Conversion of Methanol into Olefin, Spivey, J. J., Ed. The Royal Society of Chemistry, 1992, vol. 9(1), 64 pgs.
Ji, et al., "Organic-Free Synthesis of CHA-Type Zeolite Catalysts for the Methanol-to-Olefins Reaction", ACS Catalysis, 2015, vol. 5, 4456-4465.
Olsbye, et al., "Conversion of Methanol to Hydrocarbons: How Zeolite Cavity and Pore Size Controls Product Selectivity", Angew. Chem. Int. Ed., Apr. 2012, vol. 51(24), 5810-5831.

(Continued)

Primary Examiner — Elizabeth D Wood
(74) Attorney, Agent, or Firm — Baker & Hostetler LLP

(57) ABSTRACT

The present invention is directed to methods of enhancing the catalytic activities of 8-MR zeolites, the methods comprising treating a precursor 8-MR zeolite that has been prepared without the use of an organic structure directing agent and having an Si/Al ratio of less than 5, with high temperature steam for a period of time sufficient to extract at least a portion of the aluminum from the precursor zeolite framework to form a steam-treated zeolite having an Si/tetrahedral Al ratio of greater than 5, wherein the steam has a temperature in a range of from about 350° C. to about 850° C. The compositions produced by these methods and their use in catalytic reactions are also provided.

29 Claims, 26 Drawing Sheets

(56) References Cited

OTHER PUBLICATIONS

Wang, et al., "Dealumination of Zeolites—II. Kinetic Study of the Dealumination by Hydrothermal Treatment of a $NH_4NaY$ Zeolite", J. Catal., Aug. 1991, vol. 130(2), 459-470.

Wu et al., "Mesoporous SSZ-13 Zeolite Prepared by a Dual-Template Method with Improved Performance in the Methanol-to-Olefins Reaction", J. Catal., Feb. 2013, vol. 298, 27-40.

Yuen, et al., "Product Selectivity in Methanol to Hydrocarbon Conversion for Isostructural Compositions of AFI and CHA Molecular Sieves", Microporous Mater., Feb. 1994, 2(2), 105-117.

* cited by examiner

//ORGANIC-FREE SYNTHESIS OF SMALL PORE ZEOLITE CATALYSTS

CROSS REFERENCE TO RELATED APPLICATIONS

This application claims priority to U.S. Patent Application Ser. No. 62/063,593, filed Oct. 14, 2014, the contents of which are incorporated by reference in their entirety

TECHNICAL FIELD

This disclosure is directed to small pore zeolite catalysts and methods of making and using the same. The small pore (8-MR) zeolite catalysts are made without the use of organic structure-directing agents (OSDAs).

BACKGROUND

The methanol-to-olefins (MTO) reaction is an industrially viable route for making the light olefins, ethylene and propylene, using feedstocks other than petroleum (e.g., natural gas, coal, and biomass). These feedstocks may be converted to syngas and then methanol as an intermediate. The MTO reaction can be carried out over solid acid catalysts such as microporous aluminosilicate (zeolites) and silicoaluminophosphate (SAPO) molecular sieves. The industrial catalyst for the MTO reaction is SAPO-34, a small-pore SAPO molecular sieve with the chabazite (CHA) framework topology that is currently utilized in commercial MTO plants in China. Depending upon reaction conditions, SAPO-34 can convert methanol to ethylene and propylene at 85-90% selectivity. The high selectivity toward light olefins is attributed to the material's optimal acidity (acid site strength and density) as well as the topology of the CHA framework, consisting of relatively large cavities (8.35 Å×8.35 Å×8.23 Å) that are accessible through eight-membered ring (8-MR) pore openings (3.8×3.8 Å). Only small linear molecules (alcohols and linear alkenes) can diffuse through the 8-MR pores, while larger branched and aromatic compounds, including methylated aromatic intermediates, remain trapped inside the cages. Despite its success, SAPO-34 suffers the shortcoming of requiring the use of an organic structure-directing agent (OSDA) to crystallize. Aluminosilicates (zeolites) also catalyze the reaction, but synthesizing them at high Si/Al ratios that are desirable for catalytic applications typically requires the use of OSDAs. The high cost and environmental concerns associated with removal of the OSDA from the materials prior to use has generated considerable interest in developing OSDA-free synthesis methods. Although the earliest synthetic zeolites were prepared in the absence of OSDAs, using only inorganic cations as the structure-directing species, they typically have high aluminum content (Si/Al<5) and thus limited uses, particularly in applications requiring solid acidity. CHA-type zeolites can be prepared in the absence of OSDAs, but their Si/Al ratios are too low to be of use in catalyzing reactions like MTO.

The present invention is directed to solving some of these shortcomings.

SUMMARY

The present disclosure describes a method for preparing small pore zeolite catalysts without the use of OSDAs. The resulting materials may be useful for MTO as well as deNOx and other reactions. Specifically, 8-MR zeolites are synthesized in the absence of OSDAs and dealuminated post-synthetically by a combination of steam and sometimes with subsequent acid treatments. This preparation method is demonstrated on zeolites with the CHA, RHO, and KFI frameworks and is expected to be more generally applicable in preparing catalysts starting from 8-MR zeolites with other framework types.

Certain embodiments of the present invention include methods for improving the catalytic activity of 8-MR zeolites, the method comprising treating a precursor 8-MR zeolite, having an Si/Al atom ratio of less than 5, especially where the Al atoms are predominantly tetrahedral, with steam having a temperature in a range of from about 350° C. to about 850° C. for a period of time sufficient to extract at least a portion of the aluminum from the precursor zeolite framework to form a steam-treated zeolite. This steam-treatment generally results in the formation of increased mesoporous character, decreased Brønsted acid site density, and a reduced microporous volume in the steam-treated zeolite, relative to the precursor zeolite. The methods result in products having an increased ratio of silicon to tetrahedral aluminum to values greater than 5, in some cases upwards of 40 or higher, relative to the precursors. In additional embodiments, the method may further comprise washing the steam-treated zeolites with an acid so as to remove the aluminum (oxides/hydroxides) extracted from the precursor zeolite frameworks.

The present methods are operable on precursor 8-MR zeolites, surprisingly even zeolite containing only eight membered rings. Any zeolite having only 8-MR rings, or comprising 8-membered rings as the largest ring for entrance of molecules into the intracrystalline void space, including aluminosilicates substituted by boron, gallium, hafnium, iron, tin, titanium, indium, vanadium, or zirconium, appear to be amenable to the methods described herein. Zeolites having a CHA, RHO, or KFI framework have been demonstrated to work especially well.

In some embodiments, the steam is provided at at least one temperature in a range of from 350° C. to 850° C., or a sequential combination of two or more temperatures within this range. Typically, the hold times at these one or more temperatures are on the order of from 4 to 12 hours. The specific conditions which are optimal for a given precursor zeolite may vary, but the amount of experimentation needed to define these optimum conditions would not be undue to a person of skill in the art, given the present teachings.

Importantly, these inventive methods allow for the use of precursor zeolites that have been prepared without using Organic Structure Directing Agents (OSDAs). The ability to avoid the cost and environmental concerns associated with using and removing these OSDAs is a significant advantage of the inventive methods. In some cases, the precursor zeolites contain alkali, alkaline earth, or transition metal cations (e.g., e.g., $Na^+$, $K^+$, $Cs^+$) used, for example, in the preparation of the precursor zeolite. In some embodiments, at least a portion of these cations are replaced with an acidifying agent prior to exposing the precursor 8-MR zeolite to the high temperature steam. This can provide a precursor in which at least a portion of the aluminum sites in the precursor 8-MR zeolite are acid in character.

The crystalline aluminosilicate compositions prepared by the method described herein are also within the scope of the present invention, as are their functionalized derivatives and their use in a variety of catalytic processes.

In some embodiments, the crystalline aluminosilicate compositions of the present invention contain an 8-MR zeolite structure, and are prepared by the inventive methods or are independently characterized by two or more of:

(a) an atomic ratio of the silicon to tetrahedral aluminum atoms greater than 5;

(b) an atomic ratio of tetrahedral to total aluminum atoms in a range having a lower value of about 0.1, 0.12, 0.14, 0.16, 0.18, 0.2, or 0.25, and having an upper value of about 0.2, 0.3, 0.4, 0.5, or 0.6, preferably from about 0.1 to about 0.5, more preferably from about 0.12 to about 0.2;

(c) a microporous region and a mesoporous region, in which the microporous region comprises tetrahedral aluminum and the mesoporous region contains tetrahedral, pentacoordinate, and/or octahedral (hexacoordinate) aluminum;

(d) a micropore volume comprising from 0.03 to 0.15, preferably 0.03 to 0.8, cc/gram of the composition;

(e) a total Brønsted acid site density in a range of from 0.6 to 1.2, preferably 0.7 to 0.9, mmol/gram of the composition, as determined by ammonia temperature-programmed desorption; or (f) a mesoporous Brønsted acid site density in a range of from 0.1 to 4 mmol/gram of the composition, as determined by isopropylamine temperature-programmed desorption. These compositions also exhibit XRD power patterns substantially the same as 8-MR zeolites which have not been steam-treated, suggesting that the aluminum extracted from the framework, and optionally present as penta- or hexacoordinate (octahedral) aluminum, is present in an amorphous state within the zeolite framework These crystalline aluminosilicate compositions exhibit superior catalytic activity. In further embodiments, these compositions are used in methods comprising carbonylating DME with CO at low temperatures, reducing NOx with methane, cracking, dehydrogenating, MTO, oligomerizing alkenes, aminating lower alcohols (including methanol), separating and sorbing lower alkanes (e.g., C3-C6 alkanes, hydrocracking a hydrocarbon, dewaxing a hydrocarbon feedstock, isomerizing an olefin, producing a higher molecular weight hydrocarbon from lower molecular weight hydrocarbon, reforming a hydrocarbon, converting a lower alcohol or other oxygenated hydrocarbon to produce an olefin products, reducing the content of an oxide of nitrogen contained in a gas stream in the presence of oxygen, or separating nitrogen from a nitrogen-containing gas mixture by contacting the respective feedstock with the inventive zeolite composition under conditions sufficient to affect the named transformation. In particular, these catalysts outperform 8-MR zeolites that are absent the specific characteristics described for the inventive compositions in methanol to olefin (or more generally, alcohol to olefin) syntheses, both in terms of selectivity and longevity.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods of making and methods of using, processes, devices, and systems disclosed. In addition, the drawings are not necessarily drawn to scale. In the drawings:

(FIG. 6A) full isotherms; (FIG. 6B) normalized adsorption isotherms plotted on a semilogarithmic scale; and (FIG. 6C) NLDFT cumulative pore volume vs pore diameter.

(FIG. 10A) full isotherms, (FIG. 10B) normalized adsorption isotherms plotted on a semi-logarithmic scale, and (FIG. 10C) the non-local density functional theory (NLDFT) modeled cumulative pore volume vs. pore diameter.

FIGS. 19A-F shows representative MTO reaction data obtained at 400° C. for: (FIG. 19A) unsteamed H-CHA, (FIG. 19B) 500° C.-steamed CHA, (FIG. 19C) 600° C.-steamed CHA, (FIG. 19D) 700° C.-steamed CHA, (FIG. 19E) 600° C.-steamed and acid-washed CHA, and (FIG. 19F) SAPO-34.

(FIG. 20A), 400° C. (FIG. 20B), 450° C. (FIG. 20C), and 600° C. (FIG. 20D)-steamed and acid-washed CHA (CHA-S600B80A) at a reaction temperature of 450° C.

FIGS. 27A-F show time-on-stream reaction profiles obtained at 400° C. for: (FIG. 27A) as-synthesized $NH_4$—RHO; (FIG. 27B) 600° C. steamed RHO; (FIG. 27C) 700° C. steamed RHO; (FIG. 27D) 800° C. steamed RHO; (FIG. 29E) 800° C. steamed RHO at 350° C. reaction temperature; and (FIG. 27F) 800° C. steamed RHO at 450° C. reaction temperature.

DETAILED DESCRIPTION OF ILLUSTRATIVE EMBODIMENTS

Figure 1:
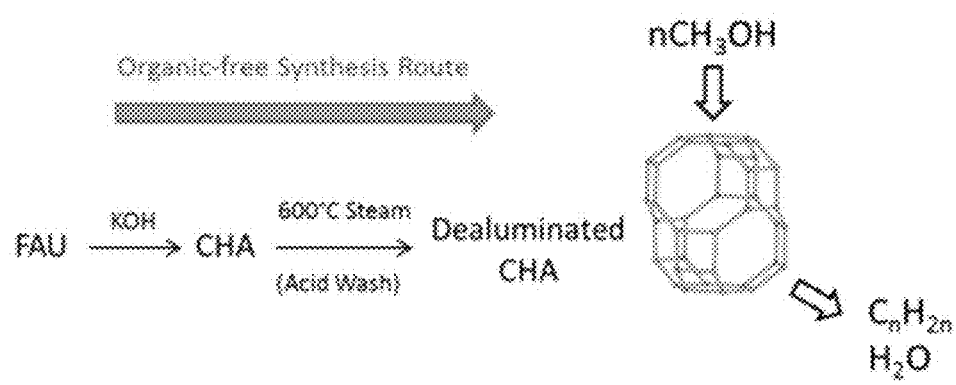
FIG. 1 shows a cartoon schematic of an embodiment of the present invention.

The present invention is directed to methods of synthesizing small pore zeolite catalysts without the use of organic structure-directing agents (OSDAs). Zeolites are synthesized in the absence of OSDAs and then modified post-synthetically by steam and sometimes with subsequent acid treatments to obtain materials that may be useful as catalysts for a number of reactions that utilize small pore zeolites (defined as pores that are made up of rings consisting of 8 tetrahedral atoms (8-MR)) such as methanol conversion to olefins and removal of NOx. The preparation method is demonstrated on 8-MR zeolites of the CHA (SSZ-13), RHO, and KFI topology, and the resulting materials are evaluated as catalysts for the methanol to olefins reaction The present invention may be understood more readily by reference to the following description taken in connection with the accompanying Figures and Examples, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and processes of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of," the basic and novel characteristic(s) of a process is the ability to provide a catalytically enhanced 8-MR zeolite starting from precursors having been prepared without OSDAs, such that the entire synthesis route of the catalytically enhanced 8-MR zeolite may be seen as "organic-free."

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Throughout this specification, words are to be afforded their normal meaning, as would be understood by those skilled in the relevant art. However, so as to avoid misunderstanding, the meanings of certain terms will be specifically defined or clarified.

"Lower alcohols" or lower alkanes refer to alcohols or alkanes, respectively, having 1-10 carbons, linear or branched, preferably 1-6 carbon atoms and preferably linear. Methanol, ethanol, propanol, butanol, pentanol, and hexanol are examples of lower alcohols. Methane, ethane, propane, butane, pentane, and hexane are examples of lower alkanes.

Unless otherwise indicated, the term "isolated" means physically separated from the other components so as to be free of solvents or other impurities; additional embodiments include those where the compound is substantially the only solute in a solvent or solvent fraction, such a analytically separated in a liquid or gas chromatography phase.

"Optional" or "optionally" means that the subsequently described circumstance may or may not occur, so that the description includes embodiments where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase "optionally isolated" means that the target material may or may not be separated from other materials used or generated in the method, and, thus, the description includes separate embodiments where the target molecule or other material is separated and where the target material is not separated, such that subsequence steps are conducted on isolated or in situ generated product.

The terms "separating" or "separated" carries their ordinary meaning as would be understood by the skilled artisan, insofar as it connotes separating or isolating the product material from other starting materials or co-products or side-products (impurities) associated with the reaction conditions yielding the material. As such, it infers that the skilled artisan at least recognizes the existence of the product and takes specific action to separate or isolate it from starting materials and/or side- or byproducts. Absolute purity is not required, though preferred, as the material may contain minor amounts of impurities and the separated or isolated material may contain residual solvent or be dissolved within a solvent used in the reaction or subsequent purification of the material.

As used herein, the term "crystalline microporous solids" or "crystalline microporous silicate or aluminosilicate solids," sometimes referred to as "molecular sieves," are crystalline structures having very regular pore structures of molecular dimensions, i.e., under 2 nm. The term "molecular sieve" refers to the ability of the material to selectively sort molecules based primarily on a size exclusion process. The maximum size of the species that can enter the pores of a crystalline microporous solid is controlled by the dimensions of the channels. These are conventionally defined by the ring size of the aperture, where, for example, the term "8-MR" or "8-membered ring" refers to a closed loop that is typically built from eight tetrahedrally coordinated silicon (or aluminum) atoms and 8 oxygen atoms. These rings are not necessarily symmetrical, due to a variety of effects including strain induced by the bonding between units that are needed to produce the overall structure, or coordination of some of the oxygen atoms of the rings to cations within the structure. As used herein, in the context of the invention, the term "8-MR" or 8-MR zeolite" refers only to those aluminosilicate crystalline materials, or optionally substituted derivatives, having frameworks comprising 8-membered rings as the largest ring for entrance of molecules into the intracrystalline void space. Exemplary structures, as identified in Baerlocher, et al., Atlas of Zeolite Framework Types, Sixth Revised Edition (2007) include one or more of ABW, ANA, BIK, BRE, CAS, CHA, EAB, EDI, EPI, ERI, ESV, GIS, GOO, JBW, KFI, LEV, LTA, MER, MON, PAU, PHI, RHO, THO, TSC, UFI, or YUG frameworks. The term "silicate" refers to any composition including silica. It is a general term encompassing, for example, pure-silica, aluminosilicate, borosilicate, or titanosilicate structures. The term "zeolite" refers to an aluminosilicate composition that is a member of this family. When described as "optionally substituted," the zeolite framework may contain boron, gallium, hafnium, iron, tin, titanium, indium, vanadium, or zirconium atoms substituted for one or more aluminum or silicon atoms in the framework. In generally, unless specifically indicated to the contrary, the zeolites of the present invention do not include the use of SAPO-type materials.

The inventive processes may be described, at least in part, in terms of hydrothermally treating a composition comprising an 8-MR zeolite made in the absence of an Organic Structure Directing Agent ("OSDA"), the precursor zeolite being selected depending on the nature of the desired product, under conditions sufficient to form the desired crystalline product, and optionally recovering and further processing the crystalline steam-treated products. Such hydrothermal treatments have previously been shown to be effective on zeolites whose frameworks contain 10- and 12-membered, but this present invention is the first disclosure that a zeolite structure containing only 8-membered rings, or whose framework comprises an 8-membered ring as the largest ring for entrance of molecules into the intracrystalline void space made without OSDAs, can be so-treated and provide a catalytically enhanced material (relative to its precursor), certainly at the Si/Al ratios claimed.

Accordingly, certain embodiments of the present invention include methods for improving the catalytic activity of 8-MR zeolites, the method comprising treating a precursor 8-MR zeolite, having an Si/Al atom ratio of less than 5, with high temperature steam for a period of time sufficient to extract at least a portion of the aluminum from the precursor zeolite framework to form a steam-treated zeolite, wherein the steam has a temperature in a range of from about 350° C. to about 850° C. In independent subsets of these embodiments, the precursor zeolite has a Si/Al atom ratio of less than 4.5, 4, 3.5, 3, or 2.5. In some of these independent subsets, precursor CHA zeolites have a Si/Al atom ratio of less than 2.5; precursor RHO zeolites have a Si/Al atom ratio of less than 3.5, less than 3, or less than 2.5; and precursor KFI zeolites have a Si/Al atom ratio of less than 3.5, less than 3, or less than 2.5. In other embodiments, practically all of the aluminum exists in the framework as tetrahedral aluminum, where the term "practically all" refers to greater than 95 atom % tetrahedral aluminum, as measured by $^{27}$Al NMR. In other embodiments, greater than 98 atom % or greater than 99 atom % of the aluminum is tetrahedral (see, e.g., FIG. 2). In such cases, the atom ratio of the Si to tetrahedral aluminum in the precursor is independently less than 5, 4.5, 4, 3.5, 3, or 2.5. As described elsewhere herein, the precursor zeolite may be optionally substituted with other framework elements, in which case, the ratios are correspondingly adjusted.

In some embodiments, the precursor 8-MR ring zeolite has a CHA, RHO, or KFI topology or framework, but any zeolite having only 8-MR rings, or whose framework comprises an 8-membered ring as the largest ring for entrance of molecules into the intracrystalline void space, including aluminosilicates substituted by boron, gallium, hafnium, iron, tin, titanium, indium, vanadium, or zirconium, appear to be amenable to the methods described herein. As described elsewhere herein, additional precursor zeolites may include those having ABW, ANA, BIK, BRE, CAS, EAB, EDI, EPI, ERI, ESV, GIS, GOO, JBW, LEV, LTA, MER, MON, PAU, PHI, THO, TSC, UFI, or YUG topologies or frameworks.

The inventive methods are flexible in that they are operable on precursor zeolites which have been prepared with or without the use of Organic Structure Directing Agents (OSDAs), and are particularly attractive for use on precursors which have been made without OSDAs. The ability of the present method to enhance the catalytic activities of these latter precursors offers a significant cost advantage relative to the preparation of comparable active materials made using OSDAs.

The use of OSDAs is well-known in zeolite synthesis, but for the sake of completeness, OSDAs are generally in the form of quaternary amines, including monoamines (e.g., isopropyltrimethyl ammonium), polyamines (e.g., hexamethylenetetramine), or even polymeric amines Where the precursor zeolites are prepared with or without such OSDAs, they can be prepared by generally recognized methods, including the use of the corresponding metal oxides, hydroxides, or alkoxides, in the presence of alkali metal, alkaline earth metal, or transition metal oxides, hydroxides, or alkoxides, often in sol-gel or other such media.

For those zeolite precursors comprising alkali, alkaline earth, or transition metal cations or oxides, such as Na$^+$, K$^+$, Cs$^+$, present, for example, as a result of the preparation of the precursor zeolite, it is preferred that at least some of these be exchanged with an acidifying agent prior to exposing the precursor 8-MR zeolite to the high temperature steam, such that at least a portion of the aluminum sites in the precursor 8-MR zeolite are acid in character before exposure to the steam. Such exchanges are conveniently accomplished by at least one, and preferably multiple washes with NH$_4^+$ or other protic source.

In processing the precursor 8-MR zeolites, the steam is provided at a temperature in a range of from 350° C. to 400° C., from 400° C. to 450° C., from 450° C. to 500° C., from 500° C. to 550° C., from 550° C. to 600° C., from 600° C. to 650° C., from 650° C. to 700° C., from 700° C. to 750° C., from 750° C. to 800° C., from 800° C. to 850° C., or a sequential combination of two or more of these ranges. The steaming conditions further include water saturation temperatures in a range of from 60° C. to 90° C., preferably 80° C. In other embodiments, the steam may be characterized as a gas stream 10-50% saturated with water vapor or water saturation pressures of about 20 to 100 kPa. The compositions may be held at these or comparable conditions for times ranging from 4 hours to 12 hours, preferably 4 to 8 hours. Again, the specific conditions described in the Examples represent specific embodiments for the CHA, RHO, and KFI materials exemplified there. Other 8-MR zeolite precursors may not be limited even to these ranges, and that the specific precursor may dictate specific temperatures, steam levels, and times. As shown in the Examples, the presence of insufficient steam or overly aggressive temperatures may cause degradation (e.g., loss of crystallinity) of the heat treated materials, but based on the teaching provided within this disclosure, the skilled artisan would be able to define the optimum conditions for any 8-MR precursor without undue experimentation.

As described herein, the methods result in changes within the precursor zeolite which include extraction of at least a portion of the aluminum from the zeolite framework. The methods also result in the formation of mesopores within the crystal lattice and an accompanying loss of micropore volume (see, e.g., Example 2.3.2, Table 2 shows a 70-80% loss in micropore volume in a CHA-type zeolite after steam-treatment. Less steam treatments will have correspondingly lesser losses of these volumes). Pore size distribution analyses from Ar physisorption data estimate the mesopore diameters to be approximately 2-6 nm in the steamed zeolites (see, e.g., FIG. 10C). Also shown in the Examples, the aluminum extracted from the zeolite framework can be shown to be present as pentacoordinate, octahedral aluminum, or both pentacoordinate and octahedral aluminum, as characterized by $^{27}$Al NMR. Moreover, the powder XRD patterns of the precursor and steam-treated zeolites, at least for the compositions tested, show that these non-tetrahedral aluminum moieties are amorphous or microcrystalline, since the steam-treated zeolites exhibit patterns substantially the same as those of the precursors; i.e., not new crystalline moieties are introduced to the compositions. See, e.g., FIGS. 7, 23, and 28).

Figure 4:
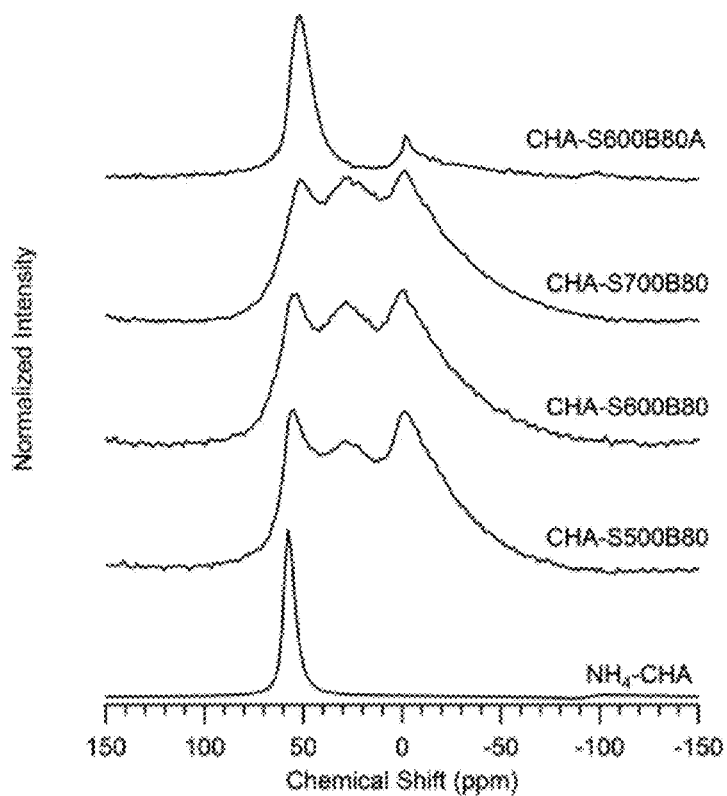
FIG. 4 shows $^{27}$Al MAS NMR spectra of the as-synthesized CHA, the CHA samples steamed at 500, 600, and 700° C. with water saturator at 80° C., and the 600° C.-steamed and acid-washed CHA (bottom to top).

The method may further comprise washing the steam-treated zeolite with acid. Such acids may include any mineral or other strong organic acid suitable for solubilizing or dissolving oxides or hydroxides of aluminum, for example HCl, H$_2$SO$_4$, H$_3$PO$_4$, or oxalic acid. Such acid washing can be used to remove at least a portion of pentacoordinate, octahedral aluminum, or both pentacoordinate and octahedral aluminum formed in the steam-treated zeolite. The ability to leach these materials out of the structures also strongly suggests that these species occupy space within the newly formed mesopores (see, e.g., Example 2.3.1; FIG. 4), such that this washing step is able to at least partially clear these mesopores.

The amount of non-tetrahedral aluminum in the steam-treated zeolites can be substantial, as measurements have shown that, in some compositions, atomic ratio of tetrahedral to total aluminum atoms in a range having a lower value of about 0.1, 0.12, 0.14, 0.16, 0.18, 0.2, or 0.25, and having an upper value of about 0.2, 0.3, 0.4, 0.5, or 0.6, preferably from about 0.1 to about 0.5, more preferably from about 0.12 to about 0.2. This corresponds to upwards of 80 to 88 atom % of the aluminum having been removed from the precursor framework.

Following the steam-treating methods, the ratio of the silicon atoms to tetrahedral aluminum atoms in the steam-treated zeolite is greater than 5 (as determined by the methods described in the Examples). In certain of these embodiments, this ratio may be in a range of from 5.1 to 5.3, from 5.3 to 5.5, from 5.5 to 6, from 6 to 6.5, from 6.5 to 7, from 7 to 7.5, from 7.5 to 8, from 8 to 9, from 9 to 10, from 10 to 12, from 12 to 14, from 14 to 16, from 16 to 18, from 18 to 20, from 20 to 24, from 24 to 28, from 28 to 32, from 32 to 36, from 36 to 40, from 40 to 48, from 48 to 56, from 56 to 64, from 64 to 72, from 72 to 80, from 80 to 100, from 100 to 120, and a combination of two or more of these ranges. Ranges defined by any of the specific ratios shown in the Examples provide additional examples of such embodiments. These ratios exist even if the Si/Al atom ratio in the bulk of the steam-treated zeolite is not substantially different than that of the precursor (see, e.g., Example 2.2, Table 1).

Additionally, steam-treating these 8-MR zeolites results in a measurable reduction in the Brønsted acid site density, relative to the precursor 8-MR zeolite, presumably due to the change in micropore/mesopore character of the steam treated material. In some embodiments, the steam-treated material may be characterized as having a Brønsted acid site density in a range of from 0.6 to 1.2 mmol/gram of the steamed zeolite, preferably from 0.7 to 0.9 mmol/gram of the steamed zeolite, as determined by ammonia temperature-programmed desorption. Again, differing steam treatments Thus far, this disclosure has been directed to the methods of treating precursor 8-MR zeolites, and some of the physical changes resulting from these treatments. It should be appreciated that any of the steam-treated products are considered within the scope of the present invention.

Moreover, the mesoporous crystalline aluminosilicate zeolites, themselves, without regard to their method of making, are also independent embodiments of the present invention. That is, in independent embodiments, the invention comprises crystalline aluminosilicate compositions comprising an 8-MR zeolite structure (in the substantial absence of other sized rings), in which the composition has, or is characterized as having two or more of:

(a) an atomic ratio of the silicon to tetrahedral aluminum atoms greater than 5;

(b) an atomic ratio of tetrahedral to total aluminum atoms in a range having a lower value of about 0.1, 0.12, 0.14, 0.16, 0.18, 0.2, or 0.25, and having an upper value of about 0.2, 0.3, 0.4, 0.5, or 0.6, preferably from about 0.1 to about 0.5, more preferably from about 0.12 to about 0.2;

(c) a microporous region and a mesoporous region, in which the microporous region comprises tetrahedral aluminum and the mesoporous region contains tetrahedral, pentacoordinate, and/or octahedral aluminum;

(d) a micropore volume comprising from 0.03 to 0.15, preferably 0.03 to 0.8, cc/gram of the composition;

(e) a total Brønsted acid site density in a range of from 0.6 to 1.2, preferably from 0.7 to 0.9, mmol/gram of the composition, as determined by ammonia temperature-programmed desorption; or (f) a mesoporous Brønsted acid site density in a range of from 0.1 to 4 mmol/gram of the composition, as determined by isopropylamine temperature-programmed desorption.

In separate independent embodiments, the invention comprises crystalline aluminosilicate compositions comprising an 8-MR zeolite structure (in the substantial absence of other sized rings), in which the composition has, or is characterized as having three or more, four or more, five or more, or all of the features (a) to (f) of the preceding paragraph.

Figure 7:
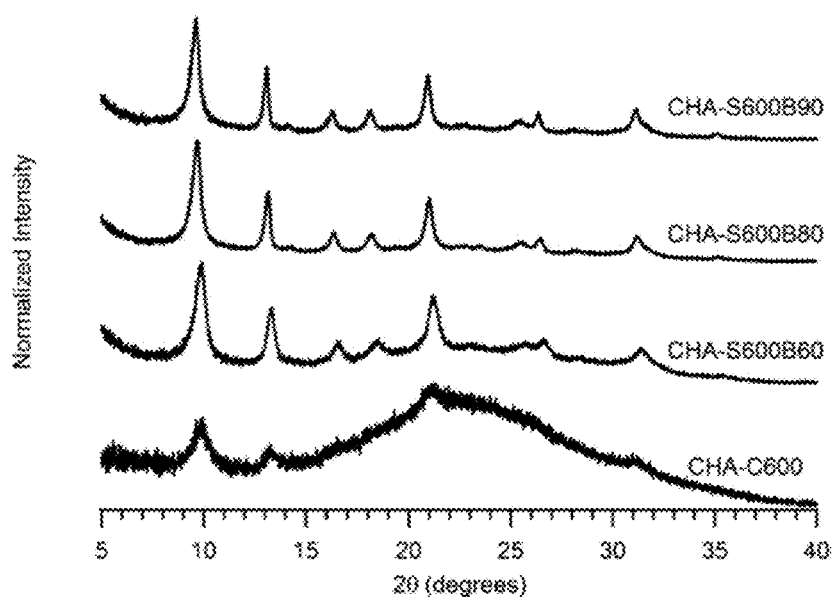
FIG. 7 shows powder XRD patterns of CHA samples steamed at 600° C. with varying partial pressures of steam.
Figure 23:
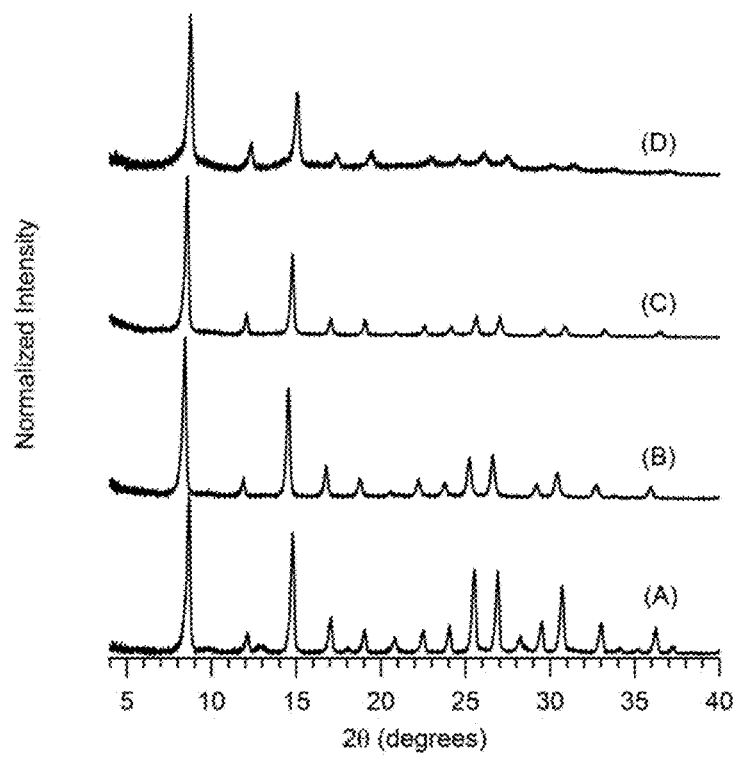
FIG. 23 shows powder XRD patterns of A) as-synthesized RHO ($NH_4^+$ form), B) 600° C. steamed RHO, C) 700° C. steamed RHO and D) 800° C. steamed RHO
Figure 28:
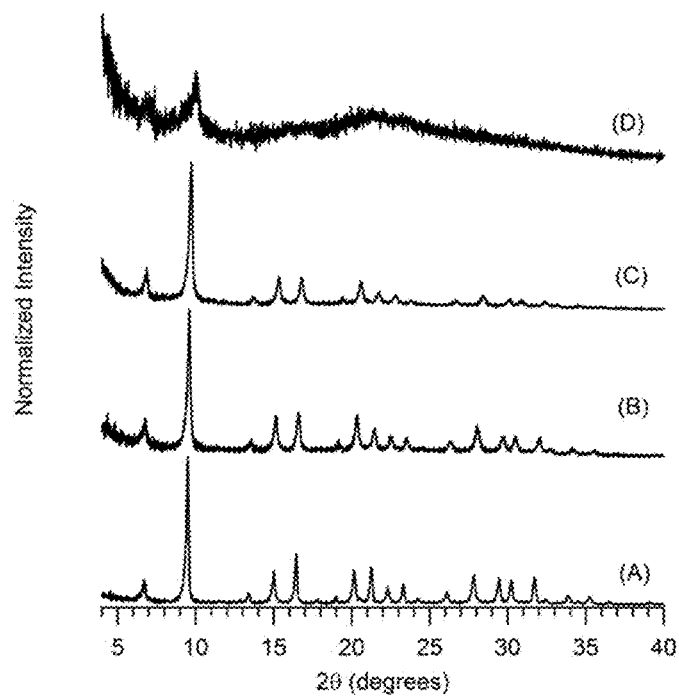
FIG. 28 shows powder XRD patterns of A) as-synthesized KFI ($NH_4^+$ form), B) 600° C. steamed KFI, C) 700° C. steamed KFI, D) 800° C. steamed KFI.

Additional embodiments include those wherein a crystalline aluminosilicate zeolite also exhibit a powder XRD pattern substantially the same as any of the 8-MR zeolites explicitly described herein, including those shown in FIGS. 7, 23, and 28. As used herein, the term "substantially the same as," in the context of these XRD patterns, is intended to accommodate instrumental errors and slight changes in lattice constants, which may amount to differences in errors in scattering angle (two theta) measurements on the order of ±0.15 degrees, and those differences associated with sample preparation. For example, crystal size will affect the shape and intensity of peaks, which can in some cases lead to significant peak broadening. Calcination can also result in changes in the intensities of the peaks as compared to patterns of the "as-made" material, as well as minor shifts in the diffraction pattern. The crystalline solids produced by exchanging the metal or other cations present in the solids with various other cations ($NH_4^+$ and then calcining to produce $H^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments. Accordingly, the skilled artisan would expect that a description that structures having XRD patterns with peaks within such small variances would still be considered within the scope of this invention.

Additionally, these inventive compositions may be further modified, for example, by incorporating hydrogenating components, such as tungsten, vanadium molybdenum, rhenium, nickel cobalt, chromium, manganese, or a noble metal, such as palladium or platinum, within the zeolite structures. For example, metals may also be introduced into these inventive zeolites by replacing some of the cations in the structures with metal cations via standard ion exchange techniques. (see, for example, U.S. Pat. No. 3,140,249 issued Jul. 7, 1964 to Plank et al.; U.S. Pat. No. 3,140,251 issued Jul. 7, 1964 to Plank et al.; and U.S. Pat. No. 3,140,253 issued Jul. 7, 1964 to Plank et al.). Typical replacing cations can include metal cations, e.g., rare earth, Group 1, Group 2 and Group 8 metals, as well as their mixtures. Cations of metals such as rare earth, Mn, Ca, Mg, Zn, Cd, Pt, Pd, Ni, Co, Ti, Al, Sn, and Fe are particularly preferred.

Following contact with the salt solution of the desired replacing cation, the inventive aluminosilicate zeolites can be typically washed with water and dried at temperatures ranging from 65° C. to about 200° C. After washing, the exchanged zeolites can be calcined in air or inert gas at temperatures ranging from about 25° C. to about 200° C. or from about 200° C. to about 850° C., as described above and depending on the nature of the calcining atmosphere, for periods of time ranging from 1 to 48 hours or more, to produce a catalytically active product especially useful in hydrocarbon conversion processes. Regardless of the cations present in the synthesized form of the crystalline microporous solid, the spatial arrangement of the atoms which form the basic crystal lattice of the crystalline solid remains essentially unchanged.

The crystalline aluminosilicate zeolites may also be treated under conditions so as to incorporate at least one type of transition metal or transition metal oxide catalyst into the pore structure, for example by vapor or chemical deposition or precipitation. As used herein, the term "transition metal" refers to any element in the d-block of the periodic table, which includes groups 3 to 12 on the periodic table. In actual practice, the f-block lanthanide and actinide series are also considered transition metals and are called "inner transition metals. Scandium, yttrium, titanium, zirconium, vanadium, manganese, chromium, molybdenum, tungsten, iron, ruthenium, osmium, cobalt, rhodium, iridium, nickel, palladium, platinum, copper, silver, gold, or mixtures thereof are preferred.

The as-synthesized or exchanged zeolite products can be formed into a wide variety of physical shapes. Generally speaking, the zeolite can be in the form of a powder, a granule, or a molded product, such as extrudate. In cases where the catalyst is molded, such as by extrusion with an organic binder, these crystalline solids can be extruded before drying, or, dried or partially dried and then extruded. The crystalline zeolites can be composited with other materials resistant to the temperatures and other conditions employed in organic conversion processes. Such matrix materials include active and inactive materials and synthetic or naturally occurring crystalline solids, including zeolites, as well as inorganic materials such as clays, silica and metal oxides.

The inventive aluminosilicate zeolites, calcined or doped or treated with the transition metal catalysts described herein may also be used as catalysts or frameworks for a variety of chemical reactions, including hydrocracking hydrocarbons, dewaxing hydrocarbon feedstocks, isomerizing hydrocarbons including olefins, producing higher molecular weight hydrocarbons from lower molecular weight hydrocarbons, converting lower alcohols and other oxygenated hydrocarbons to produce liquid products including olefins, reducing the content of oxides of nitrogen contained in a gas stream in the presence of oxygen, and separating nitrogen from a nitrogen-containing gas mixture. In each case, the processes include contacting the respective feedstock with the catalyst under conditions sufficient to affect the transformation. Such transformations and the specific conditions used in these transformations are known to those of ordinary skill in the art. Exemplary conditions for such reactions/transformations may also be found in the Examples and in WO/1999/008961, which is incorporated by reference herein in its entirety for all purposes.

In various embodiments, the crystalline microporous solids mediate or catalyze an array of chemical transformations. As follows, each of the crystalline solid materials will have utility in at least each of the following applications, though it is believed that 8-MR structures of this invention will be especially useful in converting lower alcohols and other oxygenated hydrocarbons to produce liquid products including olefins, reducing the content of oxides of nitrogen contained in a gas stream in the presence of oxygen, and separating nitrogen from a nitrogen-containing gas mixture.

Some embodiments provide processes for converting hydrocarbons, each process comprising contacting a hydrocarbonaceous feed at hydrocarbon converting conditions with a catalyst comprising a crystalline microporous solid of this invention. The crystalline material may be predominantly in the hydrogen form, partially acidic or substantially free of acidity, depending on the process.

Other embodiments provide hydrocracking processes, each process comprising contacting a hydrocarbon feedstock under hydrocracking conditions with a catalyst comprising a crystalline microporous solid of this invention, preferably predominantly in the hydrogen form.

Still other embodiments provide processes for dewaxing hydrocarbon feedstocks, each process comprising contacting a hydrocarbon feedstock under dewaxing conditions with a catalyst comprising a crystalline microporous solid of this invention, preferably predominantly in the hydrogen form.

Yet other embodiments provide processes for improving the viscosity index of a dewaxed product of waxy hydrocarbon feeds, each process comprising contacting the waxy hydrocarbon feed under isomerization dewaxing conditions with a catalyst comprising a crystalline microporous solid of this invention, preferably predominantly in the hydrogen form.

Additional embodiments include those process for producing a C20+ lube oil from a C20+ olefin feed, each process comprising isomerizing said olefin feed under isomerization conditions over a catalyst comprising at least one transition metal catalyst and a crystalline microporous solid of this invention. The crystalline microporous solid may be predominantly in the hydrogen form.

Also included in the present invention are processes for isomerization dewaxing a raffinate, each process comprising contacting said raffinate in the presence of added hydrogen with a catalyst comprising at least one transition metal and a crystalline microporous solid of this invention. The raffinate may be bright stock, and the zeolite may be predominantly in the hydrogen form.

Also included in this invention is a process for increasing the octane of a hydrocarbon feedstock to produce a product having an increased aromatics content, each process comprising contacting a hydrocarbonaceous feedstock which comprises normal and slightly branched hydrocarbons having a boiling range above about 40° C. and less than about 200° C., under aromatic conversion conditions with a catalyst comprising a crystalline microporous solid of this invention made substantially free of acidity by neutralizing said zeolite with a basic metal. Also provided in this invention is such a process wherein the crystalline microporous solid contains a transition metal component.

Also provided by the present invention are catalytic cracking processes, each process comprising contacting a hydrocarbon feedstock in a reaction zone under catalytic cracking conditions in the absence of added hydrogen with a catalyst comprising a crystalline microporous solid of this invention, preferably predominantly in the hydrogen form. Also included in this invention is such a catalytic cracking process wherein the catalyst additionally comprises a large pore crystalline cracking component.

This invention further provides isomerization processes for isomerizing C4 to C7 hydrocarbons, each process comprising contacting a feed having normal and slightly branched C4 to C hydrocarbons under isomerizing conditions with a catalyst comprising a crystalline microporous solid of this invention, preferably predominantly in the hydrogen form. The crystalline microporous solid may be impregnated with at least one transition metal, preferably platinum. The catalyst may be calcined in a steam/air mixture at an elevated temperature after impregnation of the transition metal.

In accordance with this invention there is also provided processes for isomerizing olefins, each process comprising contacting said olefin under conditions which cause isomerization of the olefin with a catalyst comprising a crystalline microporous solid of this invention.

The present invention further provides processes for oligomerizing olefins, each process comprising contacting an olefin feed under oligomerization conditions with a catalyst comprising a crystalline microporous solid of this invention.

This invention also provides processes for converting lower alcohols and other oxygenated hydrocarbons, each process comprising contacting said lower alcohol (for example, methanol, ethanol, or propanol) or other oxygenated hydrocarbon with a catalyst comprising a crystalline microporous solid of this invention under conditions to produce liquid products. Compositions having the CHA, RHO, and KPI topologies are especially useful in this regard (see, e.g., Examples 2.5.1 and 4.3; Tables 4 and 7).

Also provided by the present invention are processes for reducing oxides of nitrogen contained in a gas stream in the presence of oxygen wherein each process comprises contacting the gas stream with a crystalline microporous solid of this invention. The a crystalline microporous solid may contain a metal or metal ions (such as cobalt, copper or mixtures thereof) capable of catalyzing the reduction of the oxides of nitrogen, and may be conducted in the presence of a stoichiometric excess of oxygen. In a preferred embodiment, the gas stream is the exhaust stream of an internal combustion engine.

The following listing of embodiments is intended to complement, rather than displace or supersede, the previous descriptions.

Embodiment 1

A method for improving the catalytic activity of 8-MR zeolites, the method comprising treating a precursor 8-MR zeolite, having an Si/Al atom ratio of less than 5, 4.5, 4. 3.5, 3, or 2.5, with high temperature steam for a period of time sufficient to extract at least a portion of the aluminum from the precursor zeolite framework to form a steam-treated zeolite, wherein the steam has a temperature in a range of from about 350° C. to about 850° C.

Embodiment 2

The method of Embodiment 1, wherein the atom ratio of the silicon to tetrahedral aluminum in the steam-treated zeolite is greater than 5. In certain of these embodiments, the atom ratio of silicon to tetrahedral aluminum in the steam-treated aluminum is in a range of from 5.1 to 5.3, from 5.3 to 5.5, from 5.5 to 6, from 6 to 6.5, from 6.5 to 7, from 7 to 7.5, from 7.5 to 8, from 8 to 9, from 9 to 10, from 10 to 12, from 12 to 14, from 14 to 16, from 16 to 18, from 18 to 20, from 20 to 24, from 24 to 28, from 28 to 32, from 32 to 36, from 36 to 40, from 40 to 48, from 48 to 56, from 56 to 64, from 64 to 72, from 72 to 80, from 80 to 100, from 100 to 120, and a combination of two or more of these ranges. Ranges defined by any of the specific ratios shown in the Examples provide additional examples of such embodiments.

Embodiment 3

The method of Embodiment 1 or 2, wherein the precursor 8-MR ring zeolite has a CHA, RHO, or KFI framework. Any zeolite having 8-member rings, including those having only 8-member rings or whose framework comprises an 8-membered ring as the largest ring for entrance of molecules into the intracrystalline void space, comprising aluminosilicates substituted by boron, gallium, hafnium, iron, tin, titanium, indium, vanadium, or zirconium, are suitable to the methods described herein. Additional materials include zeolites having one or more of ABW, ANA, BIK, BRE, CAS, EAB, EDI, EPI, ERI, ESV, GIS, GOO, JBW, LEV, LTA, MER, MON, PAU, PHI, THO, TSC, UFI, and YUG topologies or frameworks.

Embodiment 4

The method of any one of Embodiments 1 to 3, wherein the precursor 8-MR ring zeolite contains aluminum in its framework, wherein practically all of the aluminum exists in the framework as tetrahedral aluminum.

Embodiment 5

The method of any one of Embodiments 1 to 4, wherein the high temperature of the steam is in a range of from 350° C. to 400° C., from 400° C. to 450° C., from 450° C. to 500° C., from 500° C. to 550° C., from 550° C. to 600° C., from 600° C. to 650° C., from 650° C. to 700° C., from 700° C. to 750° C., from 750° C. to 800° C., from 800° C. to 850° C., or a sequential combination of two or more of these ranges for a period of from 4 hours to 12 hours.

Embodiment 6

The method of any one of Embodiments 1 to 5, wherein the precursor zeolite is prepared without using Organic Structure Directing Agents (OSDAs).

Embodiment 7

The method of any one of Embodiments 1 to 6, further comprising exchanging any alkali, alkaline earth, or transition metals cations in the precursor 8-MR zeolite with an acidifying agent prior to exposing the precursor 8-MR zeolite to the high temperature steam.

Embodiment 8

The method of any one of Embodiments 1 to 7, wherein at least a portion of the aluminum sites in the precursor 8-MR zeolite are acid in character.

Embodiment 9

The method of any one of Embodiments 1 to 8, wherein the aluminum extracted from the precursor zeolite framework is pentacoordinate, octahedral aluminum, or both pentacoordinate and octahedral aluminum, as characterized by $^{27}$Al NMR.

Embodiment 10

The method of any one of Embodiments 1 to 9, wherein the atomic ratio of tetrahedral aluminum to total aluminum content in the steam-treated zeolite is in a range of having a lower value of about 0.1, 0.12, 0.14, 0.16, 0.18, 0.2, or 0.25, and having an upper value of about 0.2, 0.3, 0.4, 0.5, or 0.6, preferably from about 0.1 to about 0.5, more preferably from about 0.12 to about 0.2

Embodiment 11

The method of any one of Embodiments 1 to 10, wherein the steam-treated zeolite has a measurably higher mesopore volume than does the precursor 8-MR zeolite.

Embodiment 12

The method of any one of Embodiments 1 to 11, wherein the steam-treated zeolite has a measurably smaller micropore volume than does the precursor 8-MR zeolite (upwards of 80% less).

Embodiment 13

The method of any one of Embodiments 1 to 12, wherein the steam-treated zeolite has a micropore volume in a range of from 0.03 to 0.15, preferably 0.03 to 0.8, cc/gram of the steamed zeolite.

Embodiment 14

The method of any one of Embodiments 1 to 13, wherein the steam-treated zeolite has a measurably smaller Brønsted acid site density than does the precursor 8-MR zeolite.

Embodiment 15

The method of any one of Embodiments 1 to 14, wherein the steam-treated zeolite has Brønsted acid site density in a range of from 0.6 to 1.2 mmol/gram of the steamed zeolite, preferably from 0.7 to 0.9 mmol/gram of the steamed zeolite, as determined by ammonia temperature-programmed desorption.

Embodiment 16

The method of any one of Embodiments 1 to 15, further comprising washing the steam-treated zeolite with acid.

Embodiment 17

The method of Embodiment 16, wherein the acid wash removes at least a portion of pentacoordinate, hexacoordinate aluminum, or both pentacoordinate and hexacoordinate aluminum formed in the steam-treated zeolite.

Embodiment 18

A crystalline zeolite composition prepared by the method of any one of Embodiments 1 to 17.

Embodiment 19

A crystalline zeolite composition containing an 8-MR zeolite structure, the composition characterized by two or more of:
(a) an atomic ratio of the silicon to tetrahedral aluminum atoms greater than 5;
(b) an atomic ratio of tetrahedral to total aluminum atoms in a range of from about 0.12 to about 0.6;
(c) a microporous region and a mesoporous region, in which the microporous region comprises tetrahedral aluminum and the mesoporous region contains tetrahedral, pentacoordinate, and/or hexacoordinate aluminum;
(d) a micropore volume comprising from 0.03 to 0.15, preferably 0.03 to 0.8, cc/gram of the composition;
(e) a total Brønsted acid site density in a range of from 0.6 to 1.2, preferably 0.7 to 0.9 mmol/gram of the composition, as determined by ammonia temperature-programmed desorption; or
(f) a mesoporous Brønsted acid site density in a range of from 0.1 to 4 mmol/gram of the composition, as determined by isopropylamine temperature-programmed desorption.

Embodiment 21

A method comprising carbonylating DME with CO at low temperatures, reducing NOx with methane, cracking, dehydrogenating, MTO, oligomerizing alkenes, aminating lower alcohols (including methanol), separating and sorbing lower alkanes (e.g., C3-C6 alkanes, hydrocracking a hydrocarbon, dewaxing a hydrocarbon feedstock, isomerizing an olefin, producing a higher molecular weight hydrocarbon from lower molecular weight hydrocarbon, reforming a hydrocarbon, converting a lower alcohol or other oxygenated hydrocarbon to produce an olefin products, reducing the content of an oxide of nitrogen contained in a gas stream in the presence of oxygen, or separating nitrogen from a nitrogen-containing gas mixture by contacting the respective feedstock with the crystalline zeolite composition of Embodiment 18 or 18 under conditions sufficient to affect the named transformation.

Embodiment 22

A method comprising contacting methanol with the crystalline zeolite composition of Embodiment 18 or 19 under conditions sufficient to convert the methanol to at least one type of olefin.

Embodiment 23

The method of Embodiment 22, wherein the crystalline zeolite composition retains at least 80% of its catalytic activity to convert the methanol to at least one type of olefin for at least 2 g-methanol per gram zeolite composition (upwards of 9 g-methanol per gram zeolite composition), when reacted at a temperature in a range of 350° C. to 450° C. (and under conditions described in Example 2.5.1). This 2 g-methanol per gram zeolite composition can correspond to 1-10 hours of actual reaction time, depending on the WHSV of the reactor conditions. Subsets of this Embodiment include conversion rates, catalyst lifetimes, and product profiles of the reactions described in the Examples.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees Celsius, pressure is at or near atmospheric.

Example 1. General Methods

Example 1.1. Characterization of Products

Powder X-ray diffraction (XRD) patterns were obtained on a Rigaku MiniFlex II instrument with Cu Kα radiation ($\lambda$=1.54184 Å) at a sampling window of 0.01° and scan speed of 0.05°/min. Scanning electron microscopy/energy dispersive spectroscopy (SEM/EDS) was used to determine the morphology and bulk elemental composition of the materials and was conducted on a ZEISS 1550VP instrument equipped with an Oxford X-Max SDD energy dispersive X-ray spectrometer. Powder patterns were normalized to the highest intensity peak. Solid-state $^{27}$Al MAS NMR spectra were acquired on a Bruker AM 300 MHz spectrometer operated at 78.2 MHz using a 90° pulse length of 2 µs and a cycle delay time of 1 s. Samples were loaded in a 4 mm $ZrO_2$ rotor and spun at 12 kHz. Chemical shifts were referenced to 1 M aqueous aluminum nitrate solution.

Solid-state $^{29}Si$ MAS NMR spectra were acquired on a Bruker Avance 200 MHz spectrometer operated at 39.78 MHz with $^1H$ decoupling. A 90° pulse length of 4 μs and a cycle delay time of 60 s were used for recording. Samples were loaded in a 7 mm $ZrO_2$ rotor and spun at 4 kHz, and chemical shifts were referenced to tetramethylsilane. Reported spectra are scaled to the same maximum intensity.

Argon physisorption was conducted on a Quantachrome Autosorb iQ instrument. Prior to adsorption measurements, samples were outgassed by heating (at a rate of 10° C./min) the sample under vacuum for 1 h at 80° C., 3 h at 120° C. and 10 h at 350° C. Adsorption isotherms were collected using argon at 87.45 K using the constant dose (quasi-equilibrium) method. Micropore volumes were obtained from the adsorption branch of the isotherms using the t-plot method ($0.1<P/P_0<0.3$). Pore size analyses were obtained from the adsorption branches using the non-local density functional theory (NLDFT) model provided by Quantachrome's data reduction software (based on model of Ar at 87 K on a zeolite with cylindrical pores).

$NH_3$ and isopropylamine TPD were performed on each sample to quantify the number and accessibility of the Brønsted acid sites present. $NH_3$ TPD is able to titrate essentially all acid sites both external to and within the 8-MR pore system, while isopropylamine only accesses acid sites external to the 8-MR pore system (and in areas of mesoporosity created by the steam treatment), as isopropylamine is too large to fit within the 8-MR pores. When isopropylamine desorbs from a Brønsted acid site, it reacts with the site to form propylene and ammonia. The propylene desorption peak was integrated to determine the number of Brønsted acid sites accessible to isopropylamine The materials were pelletized, crushed, and sieved, with particles between 0.6 and 0.18 mm being retained and loaded between quartz wool beds in a continuous-flow quartz-tube reactor (part of an Altamira AMI-200 reactor). A thermocouple inserted directly into the bed monitored temperature, and a Dymaxion mass spectrometer monitored desorbing products.

Once loaded, samples were heated to 150° C. for 1 h at 10° C./min and then to 600° C. for 1 h at 10° C./min in flowing helium (50 sccm) to remove any adsorbed species. For $NH_3$ TPD, samples were then cooled to 160° C., and $NH_3$ was dosed onto each sample. After a 6 h purge in flowing argon (50 sccm) at 50° C. to remove any physisorbed $NH_3$, the sample was heated to 600° C. at a rate of 10° C./min in 30 sccm argon, while the mass spectrometer monitored desorbing products, namely, m/z=17 fragments corresponding to $NH_3$. The sample was held at 600° C. for 2 h to ensure all species had fully desorbed. For isopropylamine TPD, after the initial heating to 600° C., samples were cooled to 50° C., and isopropylamine was dosed onto each sample by means of a vapor saturator. The sample was then purged in a flow of helium (50 sccm) for 6 h before heating to 600° C. at 10° C./min, with the mass spectrometer monitoring the main propylene and $NH_3$ signals (m/z=41 and 17, respectively) formed by the decomposition reaction of the isopropylamine at Brønsted acid sites in the sample.

Example 1.2. MTO Reaction Testing

Samples used for reaction testing were approximately 200 mg of pure zeolite that had been pelletized, crushed and sieved to obtain particles between 0.6 mm and 0.18 mm. A sample was supported between glass wool beds in a tubular, continuous flow reactor. Prior to reaction, all samples were calcined in situ under a flow of breathing-grade air, during which the temperature was ramped at 1° C./min to 150° C., held for 3 h, then ramped at 1° C./min to 580° C. and held for 12 h. The reaction was conducted at 350, 400, or 450° C. with a feed of 10% methanol/inert at a WHSV of 1.3 $h^{-1}$ (where WHSV is defined as the weight of feed per hour per unit weight of catalyst loaded in the reactor. if the feed rate is 100 tons per hour to the reactor having 100 tons of catalyst loaded in the reactor, WHSV is 1.0. WHSV=(charge stock weight per hour/cat weight loaded in the reactor))

Reaction testing of unsteamed CHA was conducted on a sample in the $H^+$ form (H-CHA), which was obtained by calcining the $NH_4$—CHA in situ. Regeneration of spent catalysts was conducted in situ by heating at 1° C./min from the reaction temperature to 580° C., holding for 6 h, and then cooling at 1° C./min back to the reaction temperature, all under a flow of breathing-grade air. Conversions and selectivities are computed on a carbon mole basis, and reported selectivities are normalized by the total selectivity of the products observed.

Example 2. Chabazite Zeolites

Chabazite (CHA)-type zeolites were prepared from the hydrothermal conversion of faujasite (FAU)-type zeolites, dealuminated by high-temperature steam treatments (500-700° C.), and evaluated as catalysts for the methanol-to-olefins (MTO) reaction. The effects of temperature and partial pressure of water vapor during steaming were investigated. Powder X-ray diffraction (XRD) and Ar physisorption data showed that the steam treatments caused partial structural collapse of the zeolite with the extent of degradation increasing with steaming temperature. $^{27}Al$ MAS NMR spectra of the steamed materials revealed the presence of tetrahedral, pentacoordinate, and octahedral aluminum. $NH_3$ and isopropylamine temperature-programmed desorption (TPD) demonstrated that steaming removed Brønsted acid sites, while simultaneously introducing larger pores into the CHA materials that made the remaining acid sites more accessible. Acid washing the steamed CHA-type zeolites removed a significant portion of the extra-framework aluminum, producing an increase in the bulk Si/Al ratio as well as the adsorption volume. The proton form of the as-synthesized CHA (Si/Al=2.4) rapidly deactivated when tested for MTO at a reaction temperature of 400° C. and atmospheric pressure. CHA samples steamed at 600° C. performed the best among the samples tested, showing increased olefin selectivities as well as catalyst lifetime compared to the unsteamed CHA. Both lifetime and C2-C3 olefin selectivities are found to increase with increasing reaction temperature. At 450° C., CHA steamed at 600° C. reached a combined C2-C3 olefin selectivity of 74.2% at 100% methanol conversion, with conversion remaining above 80% for more than 130 min of time-on-stream (TOS) before deactivating. More stable time-on-stream behavior was observed for 600° C.-steamed CHA that underwent acid washing: conversion above 90% for more than 200 min of TOS at 450° C. with a maximum total C2-C3 olefin selectivity of 71.4% at 100% conversion.

Example 2.1. CHA Synthesis

SSZ-13 (CHA) was synthesized following the method reported in U.S. Pat. No. 4,544,538, at a Si/Al ratio of 5 using the N,N,N-trimethyladamantylammonium hydroxide SDA. The product was calcined, $NH_4^+$-exchanged and then steamed for 24 h at 750° C. under a flow of water vapor/inert mixture, which was accomplished by bubbling inert through a water saturator held at 75° C.

CHA type zeolite was synthesized from the hydrothermal interzeolite conversion of zeolite Y (FAU) following the method of Bourgogne et. al., U.S. Pat. No. 4,503,024. In a typical synthesis, 238 mL of deionized water was mixed with 32.2 mL of 45 wt. % aqueous potassium hydroxide solution (Aldrich) to which 30 g of zeolite Y (Zeolyst, CBV712, $SiO_2/Al_2O_3=12$) was added. The mixture was shaken for about 30 s and heated in a sealed polypropylene vessel at 100° C. for 4 days under static conditions. The recovered was recovered by centrifugation, washed with water followed by acetone, and dried overnight at 100° C. The as-synthesized product had potassium as the countercation (designated K-CHA). The $NH_4^+$ form of the product was obtained by 3 repeated ion-exchanges with 1 M aqueous ammonium nitrate solution at 90° C. for 2 h at a ratio of 100 mL of liquid per gram of solid. The product was recovered by centrifugation, washed with water followed by acetone, and dried overnight at 100° C.

Figure 2:
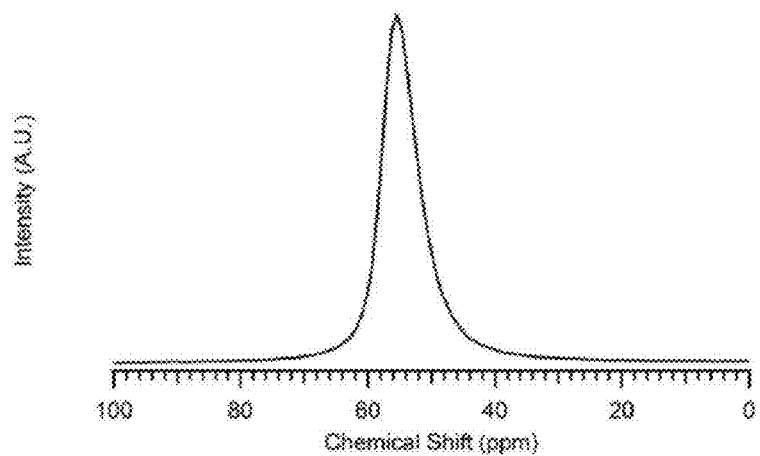
FIG. 2 shows $^{27}$Al MAS NMR spectrum of as-synthesized K-CHA

An $^{27}Al$ MAS NMR spectrum of the as-synthesized K-CHA was obtained and is shown in FIG. 2. The spectrum contains only a single sharp peak centered at approximately 55 ppm, corresponding to tetrahedral aluminum, and indicates that all aluminum was initially incorporated in the framework.

Example 2.2. Steaming and Acid Washing Treatments

Table 1 provides a summary of the steaming and acid washing treatments.

cc/min through a heated water saturator (bubbler) upstream of the furnace. Samples were steamed at temperatures of 500, 600, and 700° C. with the bubbler held at 80° C. (water saturation pressure of 47.3 kPa) and the resulting materials designated CHA-S500B80, CHA-S600B80 and CHA-S700B80, respectively. The effect of the partial pressure of steam was investigated by two additional steaming experiments at 600° C. where the bubbler temperature was changed to 60 and 90° C. (water saturation pressures of 19.9 and 70.1 kPa, respectively). For each of the bubbler temperatures tested (60° C., 80 and 90° C.), the air was approximately 50% saturated with water vapor. A dry calcination of NH4-CHA was conducted in the same tube furnace for 8 h at 600° C. (1° C./min ramp) under 50 cc/min of zero-grade air, and the product was designated CHA-C600. A portion of the CHA steamed at 600° C. with the bubbler held at 80° C. was additionally acid washed with 0.1 N aqueous hydrochloric acid at a liquid-to-solid ratio of 100:1 (w/w) for 2 h at 100° C. in a sealed vessel. The product, designated CHA-S600B80A, was recovered by filtering, washed extensively with water, and dried overnight at 100° C.

Example 2.3. Sample Characterizations

Example 2.3.1. Effect of Steaming Temperature and Acid Washing

Figure 3:
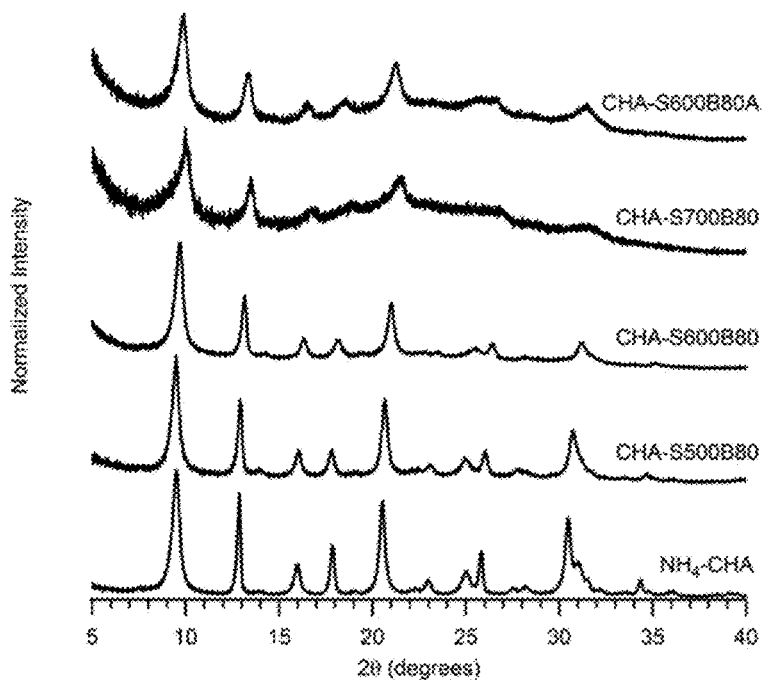
FIG. 3 shows powder XRD patterns of the as-synthesized CHA, CHA samples steamed at 500, 600, and 700° C. with water saturator at 80° C., and the 600° C.-steamed and acid-washed CHA (bottom to top).

The powder XRD patterns of the as-synthesized $NH_4$—CHA and the CHA samples steamed at 500-700° C. under the same steam partial pressure are shown in FIG. 3. The baseline signal increased relative to the peaks for the steamed samples, indicating the presence of amorphous material and a loss of crystallinity upon steaming Increasing

TABLE 1

Summary of steaming conditions, Si/Al ratios, and acid site concentrations for dealuminated CHA samples

| Entry | Sample | Steam Temp [a] ° C. | Water Saturator Temp, ° C. | Si/Al Bulk | $Si/Al_T$ [b] | Acid Site Conc. $NH_3$TPD [mmol/g] | Acid Site Conc. i-Pr-amineTPD [mmol/g] |
|---|---|---|---|---|---|---|---|
| 1 | CHA-S500B80 | 500 | 80 | 2.4 | 11 | 1.07 | 0.24 |
| 2 | CHA-S600B80 | 600 | 80 | 2.4 | 16 | 0.94 | 0.30 |
| 3 [c] | CHA-S600B80A | 600 | 80 | 7.8 | 12 | 0.80 | 0.39 |
| 4 | CHA-S700B80 | 700 | 80 | 2.3 | 17 | 0.72 | 0.20 |
| 5 | CHA-S600B90 | 600 | 90 | 2.5 | 16 | 0.84 | 0.29 |
| 6 | CHA-S600B60 | 600 | 60 | 2.4 | 15 | 0.92 | 0.16 |
| 7 | CHA-C600 | 600 | Dry calcination | 2.7 | 38 | 0.09 | 0.08 |

[a] Furnace temperature held at temperature for 8 hrs for all samples.
[b] Calculated from 27 Al NMR, AlT denotes tetrahedral Al only.
[c] Steamed sample was washed with 0.1N HCl for 2 hrs at 100° C.

Steaming was conducted under atmospheric pressure in an MTI OTF-1200X horizontal tube furnace fitted with a 3 in. ID mullite tube. $NH_4$—CHA samples (approximately 1.2 g in a typical experiment) were loaded in ceramic calcination boats and placed in the center of the tube furnace. The furnace was ramped at 1° C./min to the desired steaming temperature, held at temperature for 8 h, and then allowed to cool. The entire process was carried out under a flow of moist air that was created by bubbling zero-grade air at 50 the steaming temperature, and thus the severity of steaming, resulted in increasingly greater structural degradation, with the 700° C.-steamed sample showing the greatest loss in crystallinity. Further, the XRD peaks were shifted to lower d-spacings for the steamed samples, which can be attributed to contractions of the unit cell due to extraction of framework aluminum. The bulk Si/Al ratios of the steamed samples (Table 1) were essentially the same as that of the starting CHA (Si/Al=2.4), accommodating for minor deviations that are within measurement error. Acid washing the 600° C.-steamed CHA sample resulted in additional degradation and produced an increase in the bulk Si/Al ratio from 2.4 to 7.8.

Figure 5:
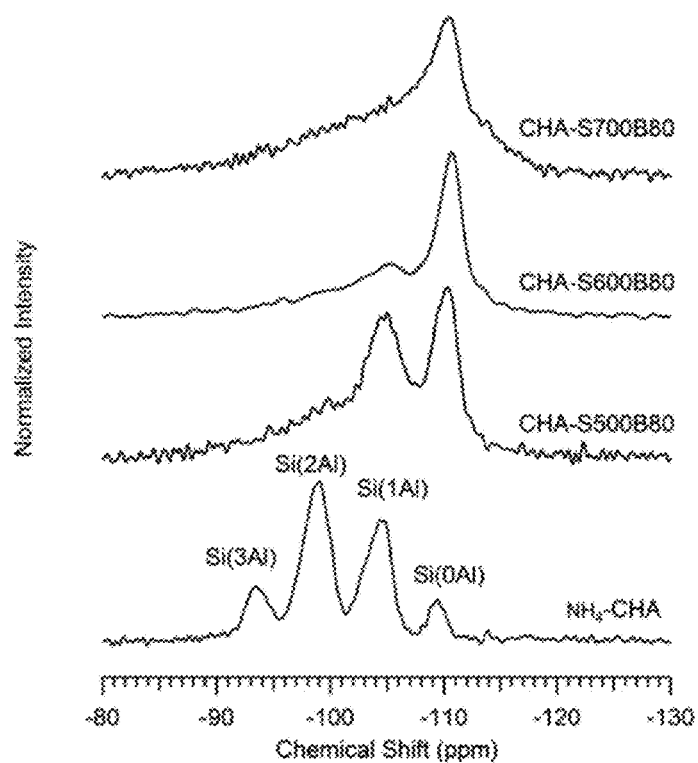
FIG. 5 shows $^{29}$Si MAS NMR spectra of the as-synthesized CHA, the CHA samples steamed at 500, 600, and 700° C. with water saturator at 80° C., and the 600° C.-steamed and acid-washed CHA (bottom to top).

Indications that aluminum was removed from the zeolite framework after the steam and acid treatments were provided by the $^{27}$Al MAS NMR spectra that are shown in FIG. 4. The spectra of both the as-synthesized K-CHA (FIG. 2) and $NH_4^+$-exchanged CHA showed a single sharp resonance centered at approximately 55 ppm, corresponding to tetrahedral, framework aluminum. In addition to this resonance, the spectra of the steamed samples showed two additional resonances centered at approximately 30 and 0 ppm that were attributed to pentacoordinate and octahedral aluminum species, respectively. As the steaming temperature was raised from 500 to 700° C., an increasing fraction of aluminum was converted from tetrahedral to pentacoordinate and octahedral (indicated by increases in the intensities of the resonances centered at 30 and 0 ppm relative to the resonance centered at 55 ppm). Accordingly, the silicon to tetrahedral aluminum (Si/AlT) ratios (Table 1), calculated from the bulk Si/Al and deconvolution of the $^{27}$Al NMR, increased with increasing steaming temperature. The intensities of the resonances associated with penta- and hexacoordinate aluminum were reduced after acid washing the 600° C.-steamed CHA, with nearly complete removal of the pentacoordinate aluminum species. These NMR data for the acid treated sample were consistent with the elemental analyses in that the bulk Si/Al increases after acid treatment. These results also suggested that the bulk of the higher-coordinated (above 4) aluminum was extra-framework. Further indication that the aluminum content of the zeolite framework changed after steaming was provided by the $^{29}$Si MAS NMR spectra (FIG. 5) of the steamed CHA. The spectrum of the as-synthesized $NH_4$—CHA showed four resonances centered at approximately −109 ppm, −104 ppm, −98 ppm, −93 ppm, that could be attributed to Si(0Al), Si(1Al), Si(2Al) and Si(3Al) environments, respectively. The silicon environment changed to predominantly Si(0Al) and Si(1Al) after steaming, with the Si(0Al) resonance becoming the largest peak.

Figure 6A:
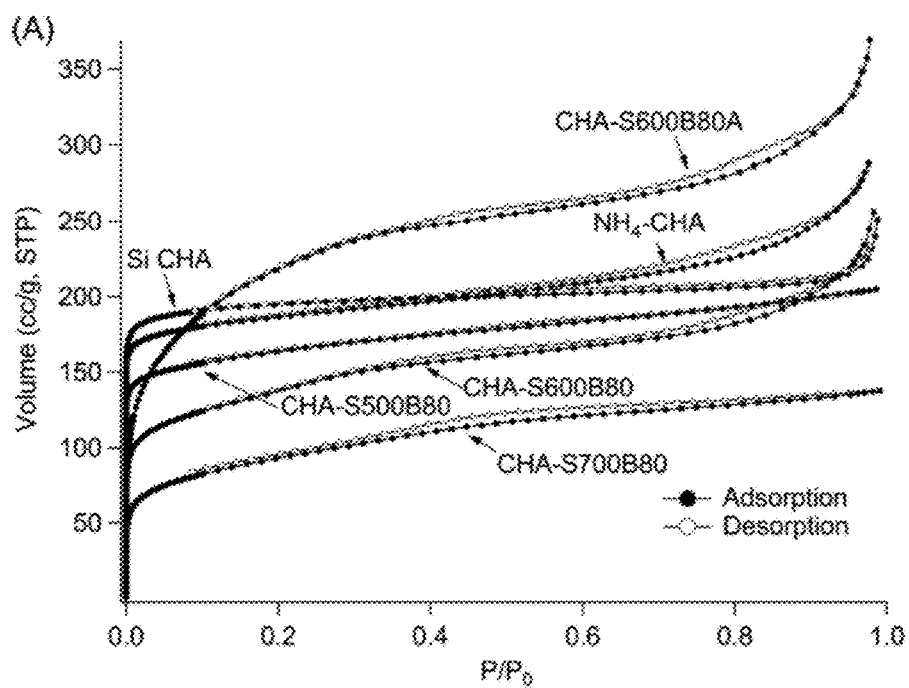
FIGS. 6A-C show Ar physisorption isotherms of the as-synthesized and 500-700° C.-steamed CHA samples, and 600° C.-steamed and acid-washed CHA.
Figure 6B:
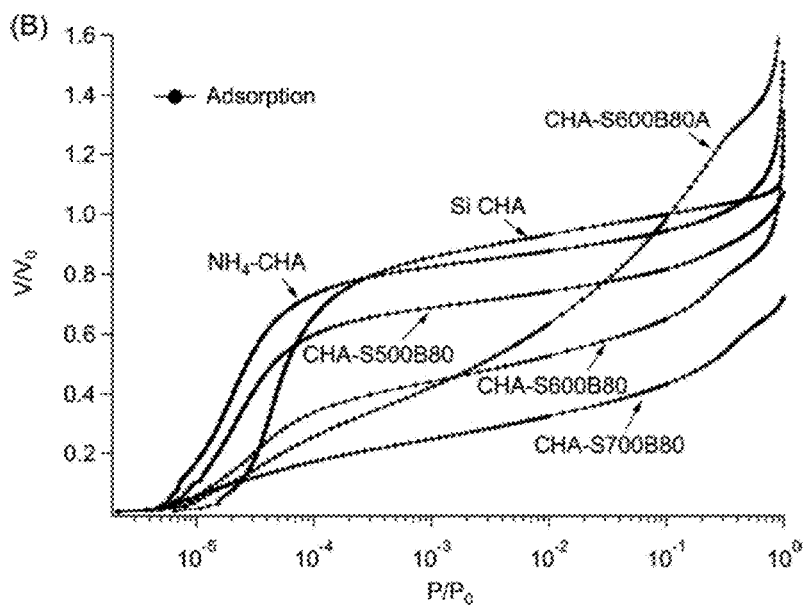

FIG. 6A shows the full Ar physisorption isotherms of the as-synthesized NH4-CHA and steamed CHA samples along with the isotherm of a pure silicon dioxide sample (Si CHA) that is used as a control for illustrating the adsorption isotherm for a pure (cation-free) CHA material. The steamed CHA samples showed decreased micropore adsorption volumes (Table 2) compared to the $NH_4$—CHA due to partial collapse of the framework. The micropore filling region is illustrated in FIG. 6B and shows the adsorption branches of the isotherms (on a semilogarithmic scale) normalized by the adsorption volume of Si CHA at $P/P_0=0.1$.

Acid washing the 600° C.-steamed CHA produced a significant increase in the adsorption volume that could be attributed to the removal of extra-framework aluminum localized within the channels and pores of the sample prior to acid leaching. This treatment, however, did not produce an increase in the micropore volume (FIG. 6B).

Figure 6C:
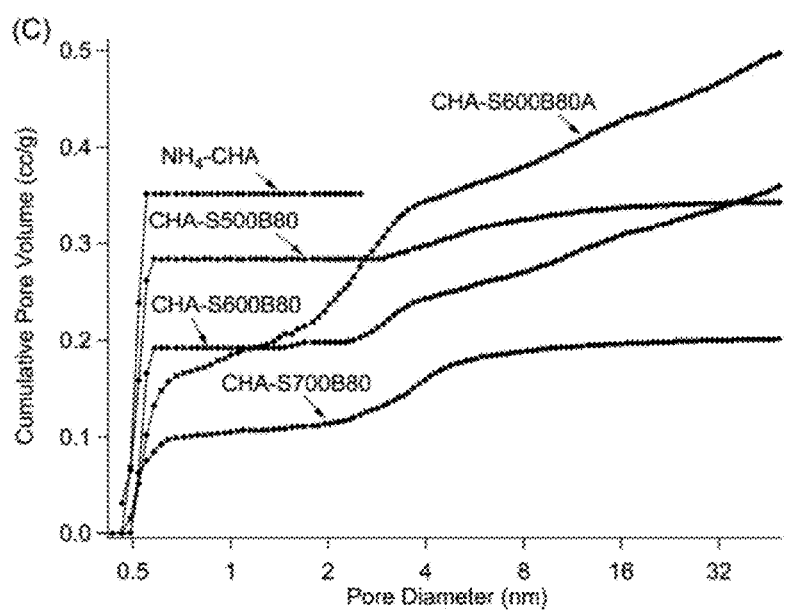

At pressures above the micropore filling $P/P_0$ range, the adsorption isotherms of the steamed samples differed in shape from that of the $NH_4$—CHA and Si CHA in that the adsorption volumes of the steamed samples increased continuously and at a higher rate per $P/P_0$ compared to the unsteamed samples. The NLDFT analyses of pore size distributions are illustrated in FIG. 6C and show the cumulative pore volumes as a function of pore diameter. All of the samples showed an initial steep increase in cumulative pore volume corresponding to micropore filling. Although the $NH_4$—CHA did not show any additional pore filling in pores larger than approximately 0.5 nm in diameter, the steamed samples showed a second step increase in cumulative pore volume for pores between 2 and 4 nm in diameter. These data suggest that mesopores were created by the steam treatments.

Entries 1, 2, and 4 of Table 1 also demonstrated how steaming decreased the total number of Brønsted acid sites from 3.75 mmol/g for the unsteamed material ($NH_4$—CHA by $NH_3$ TPD) to 1.07, 0.94, and 0.72 mmol/g for the CHA samples steamed at 500, 600, and 700° C., respectively. The number of Brønsted acid sites decreased as steaming temperature increased, consistent with increasing framework aluminum removal and degradation. These total acid site densities also correlated well with the predicted numbers based on the amount of tetrahedral aluminum remaining in each sample by $^{27}$Al NMR.

The sites accessible by isopropylamine (presumably accessible via the mesopores introduced by steaming) exhibited a maximum with increasing steaming temperature at CHA-S600B80. This result suggested that the steaming process had an optimal temperature (600° C. for CHA) before the framework degradation became too severe and access to acid sites decreased. For comparison, the unsteamed $NH_4$—CHA had 0.08 mmol/g of acid sites by isopropylamine TPD. Acid washing of the steamed CHA-S600B80 sample (Entry 3 in Table 1) revealed the presence of fewer total Brønsted acid sites but a higher fractional accessibility, as indicated by the reduced $NH_3$ and increased isopropylamine acid site counts, respectively, from the TPDs.

These TPD results were consistent with the other characterization data for the samples that suggested steaming converted tetrahedral framework aluminum to pentacoordinate or octahedral aluminum species, consequently eliminating Brønsted acid sites (as seen via $^{27}$Al NMR and NH3 TPD), and introduces mesoporosity (as seen via Ar adsorption and isopropylamine TPD). The samples steamed at 600° C. demonstrated the best balance of access to Brønsted acid sites without excessive framework degradation.

Example 2.3.2. Effect of Steam Partial Pressure

FIG. 7 shows the XRD patterns of the samples steamed at 600° C. with varying partial pressures of steam. The XRD patterns showed that lowering the steam partial pressure resulted in increased amorphization, as indicated by an increasing baseline intensity relative to the peak intensities. Almost complete collapse of the structure was observed when $NH_4$—CHA was calcined under dry air for 8 h at 600° C.

Figure 8:
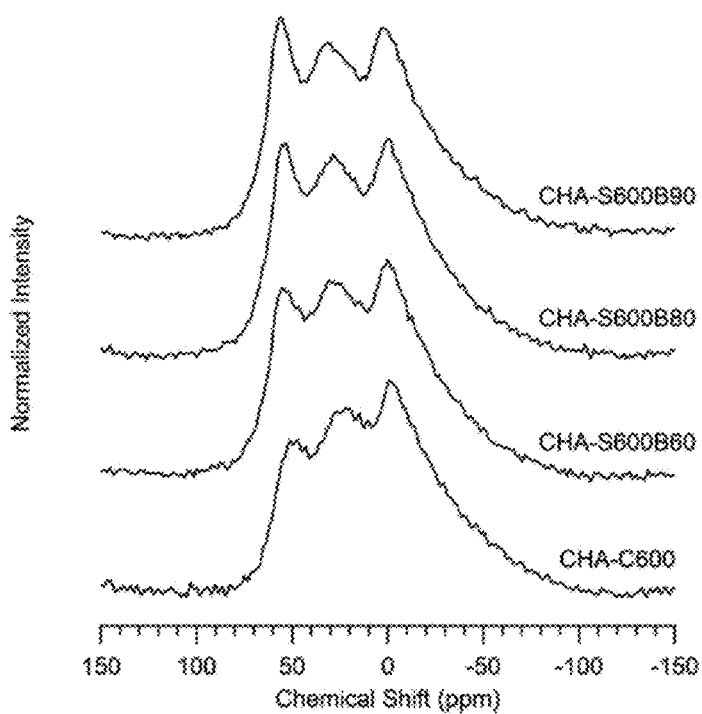
FIG. 8 shows $^{27}$Al MAS NMR spectra of CHA samples steamed at 600° C. with varying partial pressures of steam.
Figure 9:
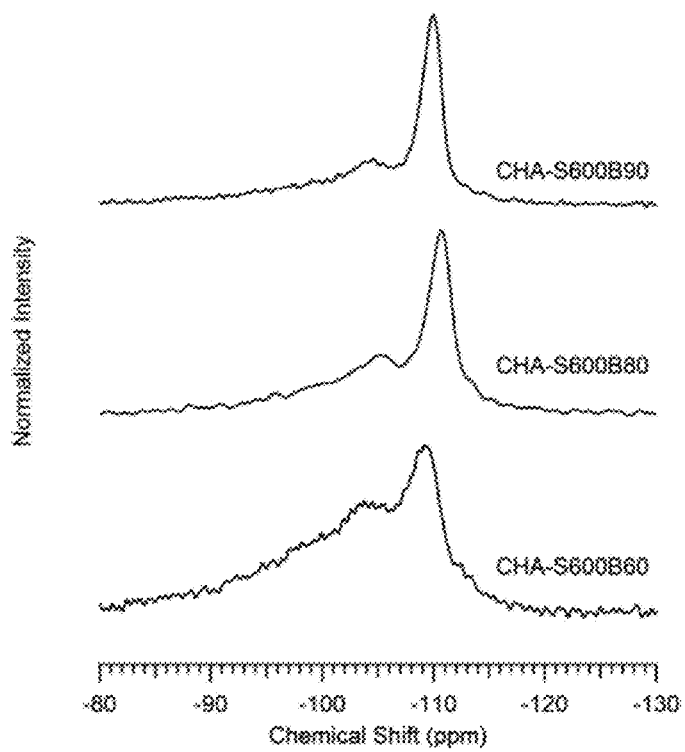
FIG. 9 shows $^{29}$Si MAS NMR spectra of CHA samples steamed at 600° C. in order of increasing steam partial pressures (bottom to top).

The $^{27}$Al NMR spectra of the steamed samples (FIG. 8), however, did not show significant differences in the relative intensities of the tetrahedral, pentacoordinate, and hexacoordinate aluminum signals, although the intensity of the tetrahedral aluminum signal relative to the higher coordinated aluminum was the lowest for the CHA calcined under dry conditions. $^{29}$Si NMR spectra of the samples steamed under varying steam partial pressures is shown in FIG. 9, which shows differences in the silicon environments for the samples steamed under varying water vapor pressures.

Figure 10A:
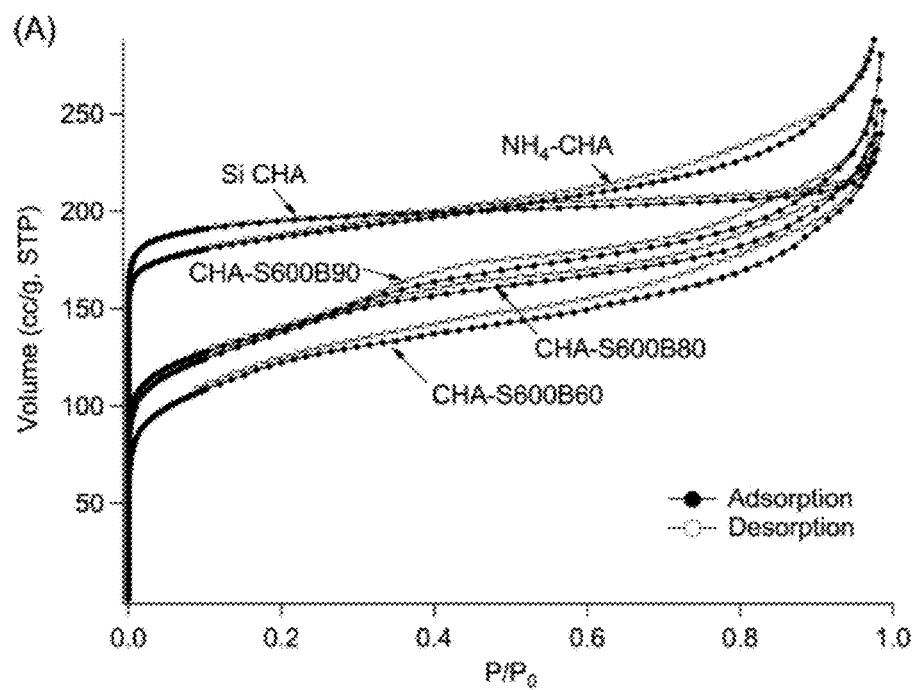
FIGS. 10A-C shows Ar physisorption isotherms of the as-synthesized and 600° C.-steamed CHA samples under varying steam partial pressures.
Figure 10B:
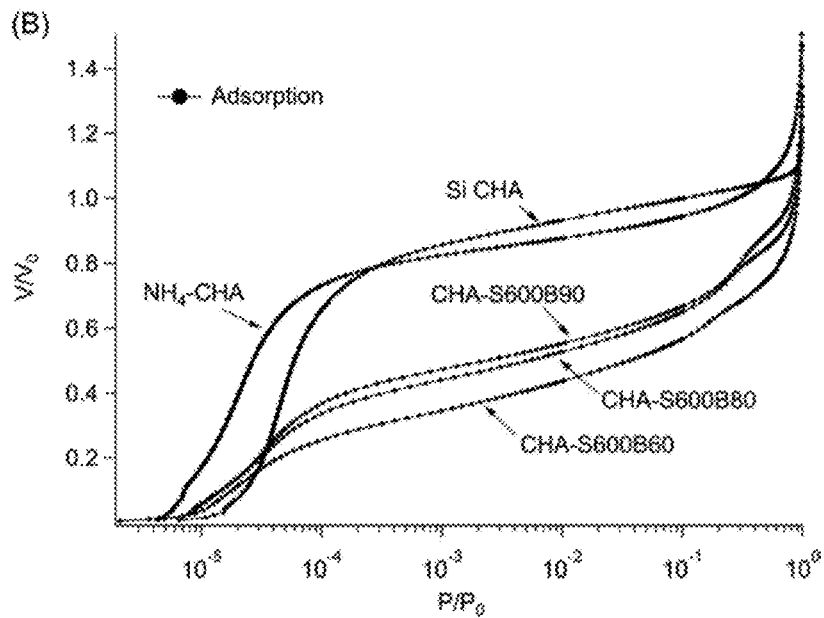
Figure 10C:
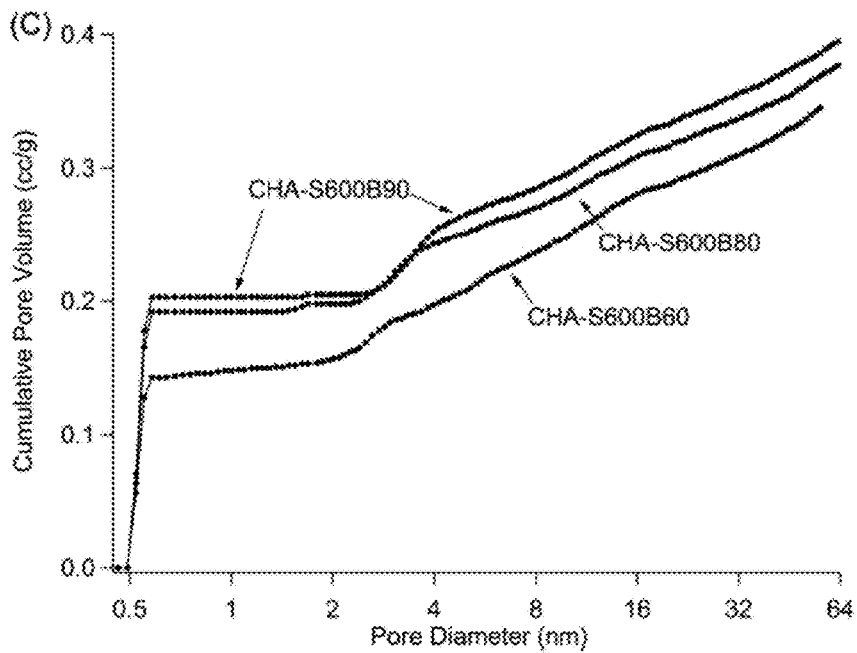

Ar physisorption measurements on the steamed samples (FIG. 10A) showed that with decreasing steam partial pressure, the samples showed decreasing adsorption volume. This trend was also observed in the micropore filling region of the isotherms (FIG. 10B) and corroborated by the intact micropore volumes (Table 2). FIG. 10C indicates that the steamed samples had essentially the same pore size distribution, showing a large step increase in cumulative pore volume for pores of 2 nm in diameter and larger.

TABLE 2

Micropore Volumes of the As-Synthesized and Steamed CHA

| sample | micropore volume (cc/g) |
|---|---|
| pure Si CHA | 0.221 |
| NH$_4$—CHA | 0.190 |
| CKA-S500B80 | 0.149 |
| CHA-S600B80 | 0.0765 |
| CHA-S700B80 | 0.0379 |
| CHA-S600B60 | 0.0466 |
| CHA-S600B90 | 0.0753 |

Interestingly, as steam partial pressure decreased, the total Brønsted acid sites titrated by NH$_3$ TPD remain relatively similar (Entries 2, 5, and 6 in Table 1, consistent with the $^{27}$Al NMR results), with a maximum value at CHA-S600B80. The isopropylamine TPD results were quite different, however, with the greatest accessibility observed for the two samples that were steamed with the water saturator at 80 and 90° C. (CHAS600B80 and CHA-S600B90, respectively). The sample with the lowest steam partial pressure, CHA-S600B60, had approximately half the isopropylamine accessibility of these other samples.

Figure 14:
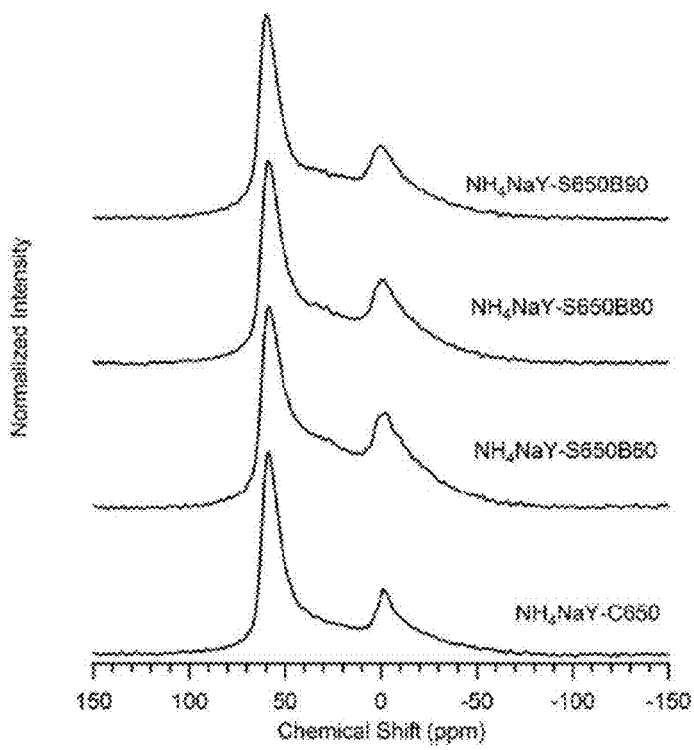
FIG. 14 shows $^{27}$Al NMR spectra of $NH_4NaY$ samples steamed for 3 h at 650° C. in order of increasing steam partial pressure (bottom to top).
Figure 15:
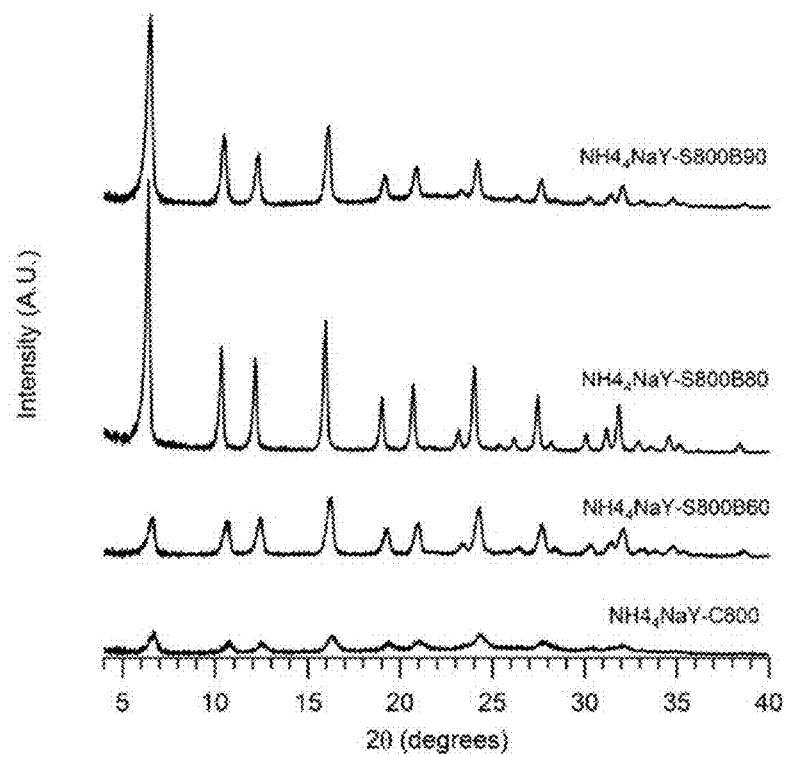
FIG. 15 shows powder XRD patterns of $NH_4NaY$ samples steamed for 8 h at 800° C. in order of increasing steam partial pressure (bottom to top).
Figure 16:
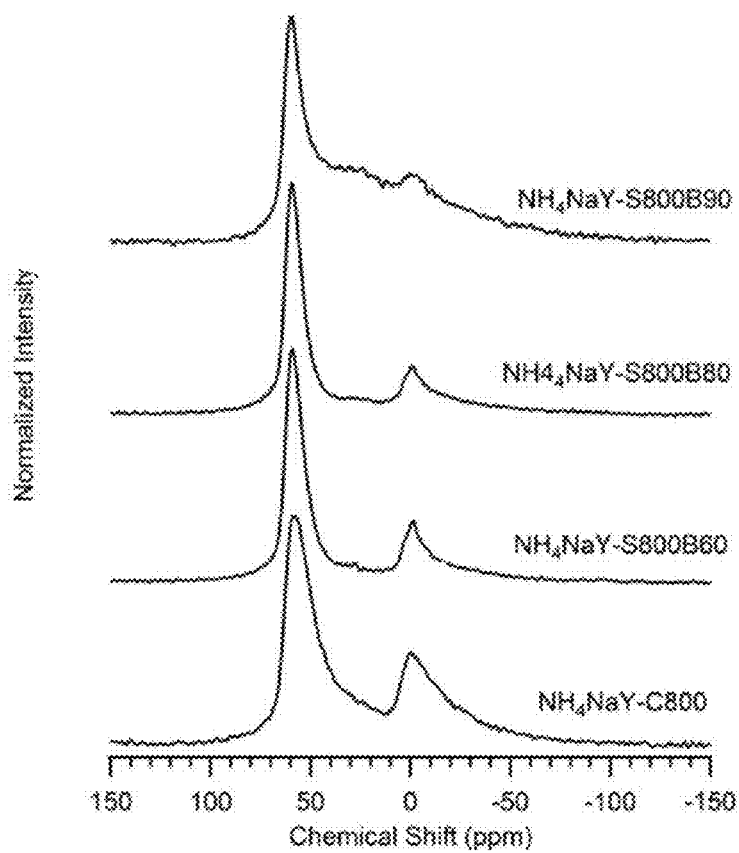
FIG. 16 shows $^{27}$Al MAS NMR of $NH_4Na$—Y samples steamed for 8 h at 800° C. in order of increasing steam partial pressure (bottom to top).

The trend of increased degradation with decreasing steam partial pressure was opposite of what has been reported for larger pore zeolites such as zeolite Y (FAU)18,19 and ZSM-5 (MFI). The steaming experiments in this present work with zeolite Y at 550 and 650° C. using a similar steam procedure to those reported by others are consistent with the literature results in that zeolite Y samples calcined in the presence of steam undergo greater dealumination compared to samples calcined in dry air. Characterizations (powder XRD patterns and $^{27}$Al NMR) for the 550 and 650° C.-steamed zeolite Y samples are provided in Table 3 and FIGS. 11 to 14. However, when zeolite Y was steamed under more severe conditions (8 h at 800° C.) using the same steaming procedure that was used with the CHA zeolites, the results in Table 3 and FIGS. 15 and 16 show the reversed trend of greater degradation with decreasing steam partial pressure, consistent with the behavior of the CHA zeolites. Furthermore, steam treatment of CHA at milder conditions (3 h at 500° C.) using the 550 and 650° C. Y steaming procedure produced increasing dealumination with increasing steam partial pressure (see Table 3 and FIGS. 17 and 18), consistent with the behavior of zeolite Y at the lower steaming temperatures. The similar behaviors between CHA and zeolite Y at these steaming conditions suggested that the trend reported here was not unique to CHA.

It has been proposed that the steaming involves hydrolyses of Al—O—Si bonds by water vapor at high temperatures, resulting in extra-framework aluminum species and the formation of vacant silanol nests. As an increasing number of the framework aluminum is extracted, portions of the zeolite collapse, forming amorphous regions. Investigations on the steam dealumination of Y zeolites further suggest that in the presence of steam, silicon may migrate in the form of orthosilicic acid (H$_4$SiO$_4$) to fill in the aluminum vacancies and thus "heal" the structure so that the resulting structure shows increased thermal stability. A similar stabilization process may be occurring during the heating period for the zeolites studied here. When heated to temperatures at which the zeolite normally became amorphous under dry conditions (600° C. for CHA and 800° C. for Y in this study), the presence of steam provided stabilization of the structure. Due to the slow ramp rate (1° C./min) used during the steaming experiments for CHA and Y where the reversed trend of increased degradation with decreasing steam partial pressure was observed, the samples spend approximately the first half of the duration of the steaming experiment in heating under a steam atmosphere. A significant portion of the steaming process would thus occur in the heating period, during which the dealumination and healing steps described above were occurring at the same time. Under the higher steam partial pressures tested, healing of the framework may be facilitated and occurred at a rate that was fast enough to compensate for the dealumination process; thus, the structure is stabilized during the heating period. At a low steam partial pressure, the rate of healing could be too slow to compensate for dealumination and dehydroxylation, and thus, significant loss of crystallinity occurs. The $^{29}$Si NMR of the samples steamed under varying steam partial pressures suggest that as the steam partial pressure is increased, the Si(0Al) peak grows in intensity relative to the downfield peaks, which would be consistent with increasing formation of Si—O—Si bonds with increasing availability of water during steaming Example 2.4. Additional Steaming Experiments with Zeolite Y and CHA Three additional sets of steaming experiments were conducted using zeolite Y (FAU), for the purposes of verifying that the steaming and dry calcination results previously reported in the literature on Y could be reproduced as well as determining whether the trend observed with CHA under varying partial pressures is also observed in Y when steamed using the same procedure. For all of the Y steaming experiments, the starting zeolite was a commercial NaY with Si/Al=2.97 that had been NH$_4^+$ exchanged three times for 2 h at 90° C. with 1 M NH$_4$NO$_3$. The NH$_4^+$ exchanged Y, designated NH$_4$NaY, had a Na/Al ratio of 0.28 (measured by EDS) and was steamed using the same tube furnace set up as that used for the CHA samples.

A summary of the steaming conditions is provided in Table 3. Two sets of steaming experiments were conducted at 550° C. and 650° C. under similar conditions reported by Wang et al. *J. Catal.*, 1991, 130, 459-470, who has investigated the effect of the water partial pressure on steaming of zeolite Y. Samples were heated at 5° C./min to the steaming temperature (550° C. or 650° C.) under 50 cc/min of dry air and then subjected to flowing steam (created by bubbling 50 cc/min of dry air through a heated water saturator) for 3 hr at the steaming temperature. Samples were cooled under 50 cc/min of dry air flow at the end of the 3 hr steaming period. Steaming experiments were conducted with the bubbler (providing approximately a 50% saturated air and water vapor mixture) held at 60° C., 80° C. and 90° C., for which the water saturation pressures are 19.9 kPa, 47.3 kPa and 70.1 kPa, respectively. An additional dry calcination was carried out on the NH$_4$NaY using the same temperature profile under flowing dry air (50 cc/min) In the third set of steaming experiments, NH$_4$NaY samples were steamed under more severe conditions using the same procedure that was used for the CHA samples steamed at 600° C. under varying steam partial pressures. Samples were heated at 1° C./min to 800° C. and held for 8 h at the steaming temperature. The entire process, including heating and cooling, was carried out under flowing air. An additional dry calcination was conducted under 50 cc/min of dry air using the same temperature profile.

To determine whether CHA would also show the same trend that was observed with Y steamed at 550° C. and 650° C., an additional series of steaming experiments was conducted with CHA using the same steaming procedures that were used for the 550° C. and 650° C. zeolite Y steaming experiments, where NH4-CHA samples were steamed for 3 h at 500° C. under varying steam partial pressures. The furnace was ramped at 5° C./min to 500° C. under 50 cc/min of dry air, steam was introduced for 3 h at 500° C. only, and the sample was then allowed to cool under flowing dry air (50 cc/min)

were very similar to each other, the $^{27}$Al NMR spectra indicated that as the steam partial pressure was increased, an increasing portion of the tetrahedral aluminum was converted to pentacoordinate and octahedral aluminum and is consistent with what was observed for the 550° C. and 650° C. steamed Y.

Example 2.5. MTO Reaction Testing

Example 2.5.1. Effect of Steaming Temperature and Acid Washing

FIGS. 19A-F illustrate representative TOS reaction data obtained at 400° C. for the as-synthesized CHA, the CHA

TABLE 3

Summary of zeolite Y steaming conditions

| Sample | Heating Ramp Rate | Steaming Time | Steaming Temperature | Bubbler Temperature | Duration of Flowing Steam | $Al_T/Al_{Total}$ |
|---|---|---|---|---|---|---|
| NH$_4$NaY-S550B90 | 5° C./min | 3 h | 550° C. | 90° C. | At steaming temperature only | 0.144 |
| NH$_4$NaY-S550B80 | 5° C./min | 3 h | 550° C. | 80° C. | At steaming temperature only | 0.288 |
| NH$_4$NaY-S550B60 | 5° C./min | 3 h | 550° C. | 60° C. | At steaming temperature only | 0.387 |
| NH$_4$NaY-C550 | 5° C./min | 3 h | 550° C. | — | Dry calcination | 0.822 |
| NH$_4$NaY-S650B90 | 5° C./min | 3 h | 650° C. | 90° C. | At steaming temperature only | 0.394 |
| NH$_4$NaY-S650B80 | 5° C./min | 3 h | 650° C. | 80° C. | At steaming temperature only | 0.325 |
| NH$_4$NaY-S650B60 | 5° C./min | 3 h | 650° C. | 60° C. | At steaming temperature only | 0.308 |
| NH$_4$NaY-C650 | 5° C./min | 3 h | 650° C. | — | Dry calcination | 0.444 |
| NH$_4$NaY-S800B90 | 1° C./min | 8 h | 800° C. | 90° C. | Entire period | 0.230 |
| NH$_4$NaY-S800B80 | 1° C./min | 8 h | 800° C. | 80° C. | Entire period | 0.670 |
| NH$_4$NaY-S800B60 | 1° C./min | 8 h | 800° C. | 60° C. | Entire period | 0.713 |
| NH$_4$NaY-C800 | 1° C./min | 8 h | 800° C. | — | Dry calcination | 0.234 |
| CHA-S500B90 | 5° C./min | 3 h | 500° C. | 90° C. | At steaming temperature only | 0.139 |
| CHA-S500B60 | 5° C./min | 3 h | 500° C. | 60° C. | At steaming temperature only | 0.156 |
| CHA-C500 | 5° C./min | 3 h | 500° C. | — | Dry calcination | 0.201 |

Figure 11:
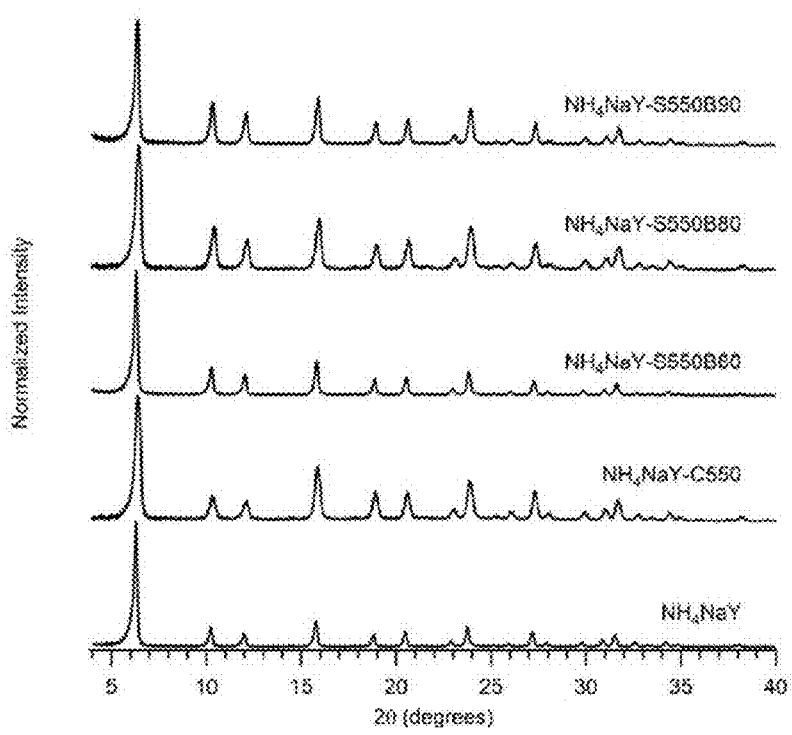
FIG. 11 shows powder XRD patterns of unsteamed $NH_4NaY$ and $NH_4NaY$ samples steamed for 3 h at 550° C. in order of increasing steam partial pressure (bottom to top).
Figure 12:
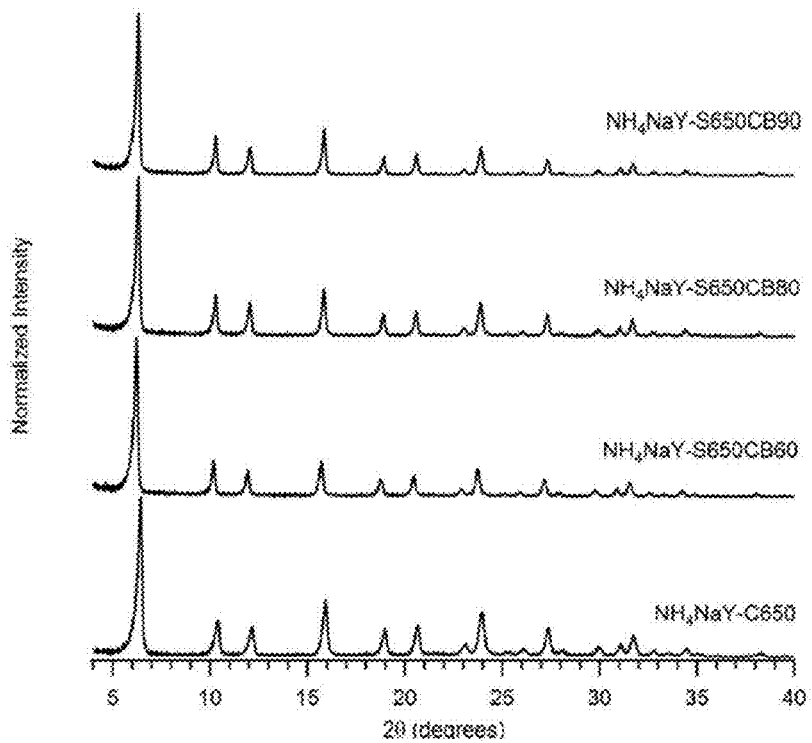
FIG. 12 shows powder XRD patterns of $NH_4NaY$ samples steamed for 3 h at 650° C. in order of increasing steam partial pressure (bottom to top).
Figure 13:
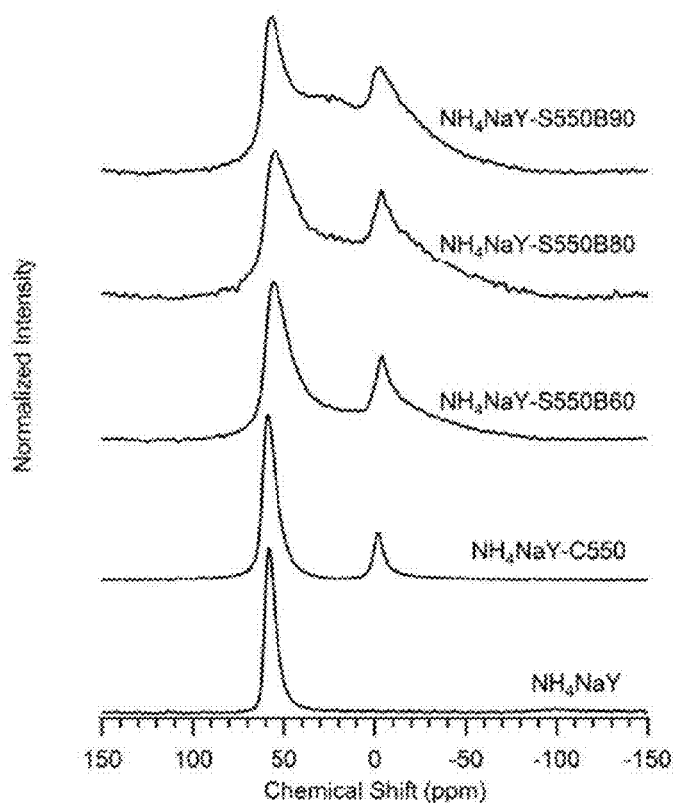
FIG. 13 shows $^{27}$Al NMR spectra of unsteamed $NH_4NaY$ and $NH_4NaY$ samples steamed for 3 h at 550° C. in order of increasing steam partial pressure (bottom to top).

FIGS. 11 and 12 show the powder XRD patterns of the NH$_4$NaY samples steamed at 550° C. and 650° C., respectively. $^{27}$Al MAS NMR spectra of the 550° C. and 650° C. steamed samples are shown in FIGS. 13 and 14. At both steaming temperatures, the $^{27}$Al NMR indicated that a greater fraction of tetrahedral aluminum was converted to pentacoordinate and octahedral aluminum for the steamed NH$_4$NaY samples compared to the dry calcined samples, consistent with what has been reported by Wang.

The powder XRD patterns and $^{27}$Al NMR spectra of the NH$_4$Na—Y samples steamed at 800° C. are shown in FIGS. 15 and 16, respectively. At these conditions, the NH$_4$NaY samples showed increased degradation when the water partial pressure was lowered, with the sample calcined under dry air showing the greatest degradation. The $^{27}$Al NMR is consistent with the XRD data in that the amount of pentacoordinate and octahedral aluminum increased relative to the tetrahedral aluminum as the water partial pressure was lowered. This trend was opposite of what was observed for the 550° C. and 650° C. steamed NH$_4$NaY, but consistent with the behavior of CHA steamed at 600° C. under varying steam partial pressures. The similarity in the behavior of steamed Y compared to CHA at these conditions suggested that the trend of increased degradation with decreasing steam partial pressure was not unique to CHA.

Figure 17:
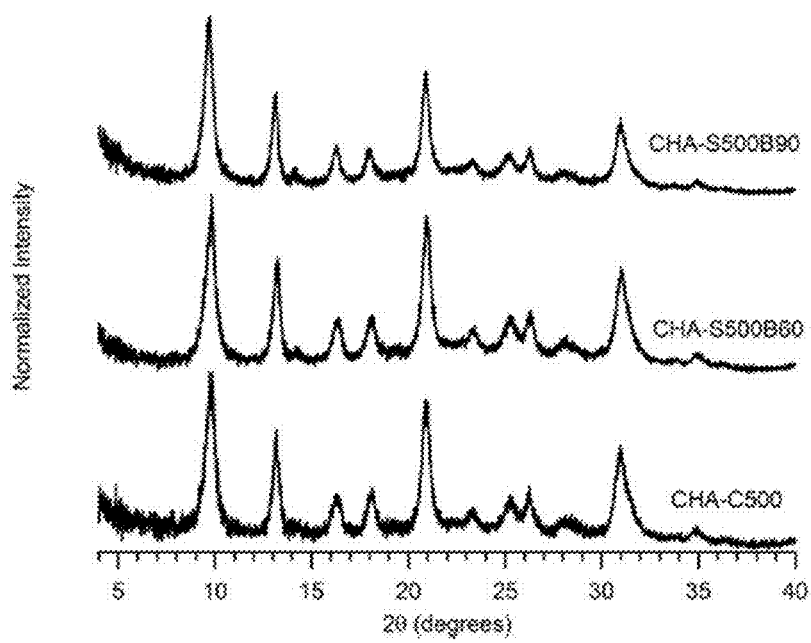
FIG. 17 shows powder XRD patterns of CHA samples steamed for 3 h at 500° C. in order of increasing steam partial pressure (bottom to top).
Figure 18:
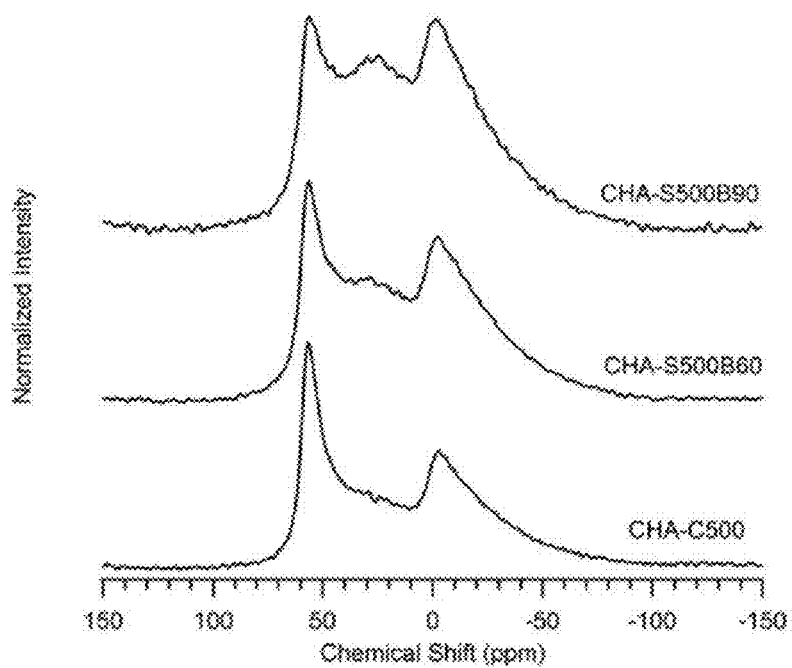
FIG. 18 shows $^{27}$Al MAS NMR of CHA samples steamed for 3 h at 500° C. in order of increasing steam partial pressure (bottom to top).

FIGS. 17 and 18 showed the powder XRD patterns and $^{27}$Al MAS NMR, respectively, of the CHA samples steamed at 500° C. where steam was introduced at 500° C. only. While the powder XRD patterns of the steamed samples samples steamed at 500-700° C. with the water saturator at 80° C., and a SAPO-34. Each of the catalysts is initially active in producing C2-C4 olefins when methanol conversion is close to 100%. With increasing TOS, methanol conversion decreases, and is accompanied by a decrease in olefin selectivities and a simultaneous increase in dimethyl ether (DME) production. C3-C5 alkanes, mainly propane and butane, are also observed among the products at the start of the reaction, with selectivities decreasing with increasing TOS. Lower alkanes (methane and ethane) are not observed among the products.

Table 4 provides a summary of the reaction data that includes the maximum methanol conversion, maximum combined C2-C3 olefin selectivity at maximum conversion and the approximate time to deactivation (arbitrarily defined as the first time point where the conversion drops below 80%). The as-synthesized CHA, while initially active in producing ethylene and propylene, has the shortest catalyst lifetime. Methanol conversion starts at 100%, but decreases rapidly after approximately 45 min (0.93 g-MeOH/g-cat) TOS, and DME becomes the main reaction product. The fast deactivation may be attributed to the high framework aluminum content of the as-synthesized CHA (Si/Al=2.4) that leads to rapid coke deposition.

TABLE 4

Maximum Combined C2—C3 Olefin Selectivities near Complete Conversion, and Deactivation Times of Catalysts Tested

| Sample | Reaction Temp., °C. | Max. MeOH Conversion | Combined C2—C3 Olefin Selectivity at Max. MeOH Conversion, % | Time to Degradation (g-MeOH/g-cat),[a] |
|---|---|---|---|---|
| H—CHA | 400 | 100.0% | 59.0 | 1.3 |
| CHA-S500B80 | 400 | 100% | 55.3 | 1.6 |
| CHA-S600B80 | 350 | 98.6% | 58.6 | 1.2 |
|  | 400 | 100.0% | 65.6 | 2.3 |
|  | 450 | 100.0% | 74.2 | 3.2 |
| CHA-S700B80 | 400 | 97.4% | 58.8 | 1.4 |
| CHA-S600B80A | 400 | 94.4% | 58.9 | 5.0 |
|  | 450 | 100.0% | 71.4 | >9.0 |
| SAPO-34 | 400 | 100.0% | 86.3 | >9.8 |

[a] First time point where MeOH conversion dropped below 80% At a MeOH WHSV of 1.3 h⁻¹ used for reaction testing, the actual time-on-stream for conversion to drop below 80% corresponds to a time of about 1-4 hours Whereas deactivation occurs abruptly for the as-synthesized CHA, the steamed materials show more gradual deactivation profiles that vary depending on the severity of steaming CHA steamed at 500° C. has a slightly improved lifetime compared to the as-synthesized CHA. Methanol is initially completely converted and remains above 80% conversion for 64 min (1.3 g-MeOH/g-cat) TOS. However, olefin selectivities for CHA-S500B80 are comparable to the unsteamed CHA.

Figure 24:
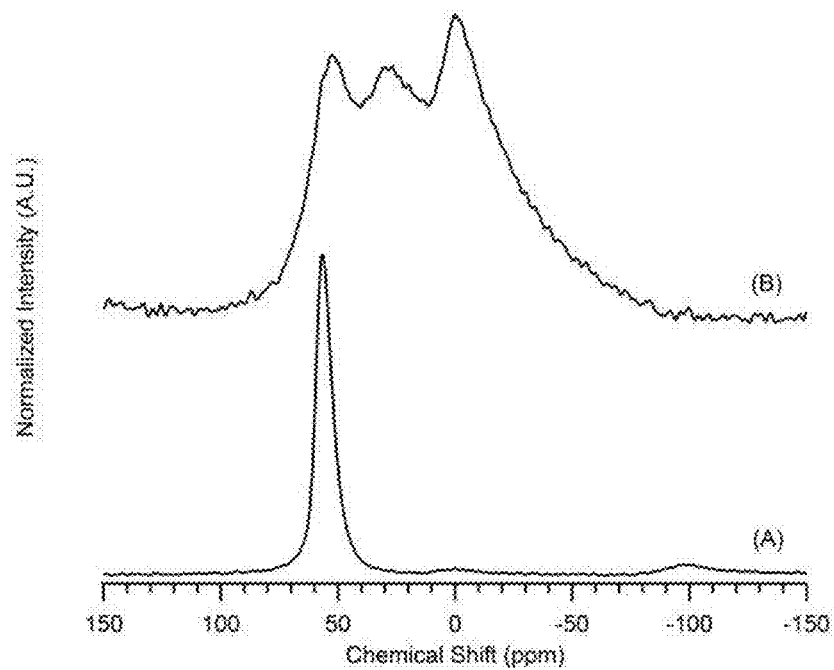
FIG. 24 shows an $^{27}Al$ MAS NMR spectrum of A) as synthesized RHO ($NH_4^+$ form) and B) 700° C. steamed RHO.
Figure 25:
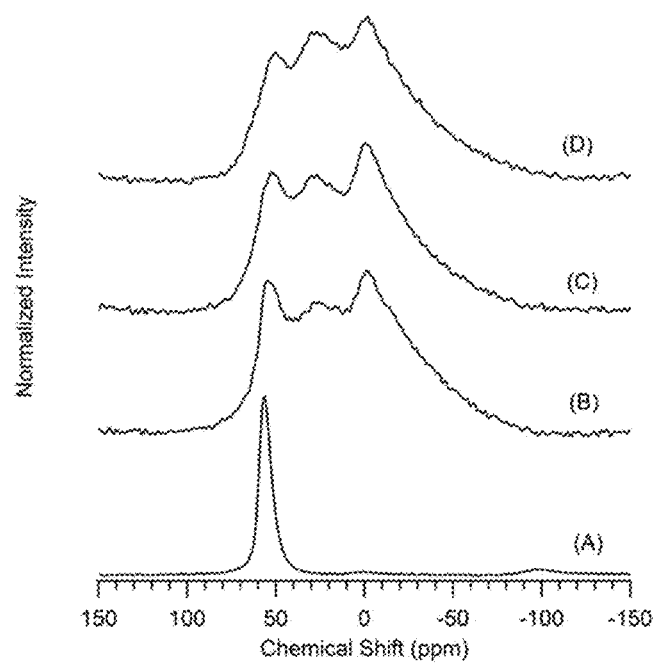
FIG. 25 shows $^{27}Al$ NMR of A) as-synthesized RHO ($NH_4^+$ form), B) 600° C. steamed, C) 700° C. steamed, and D) 800° C. steamed RHO.

CHA steamed at 600° C. shows the most stable reaction profile and longest lifetime among the steamed samples. Methanol conversion starts at 100% and remains above 80% for more than 92 min (2.0 g-MeOH/g-cat) TOS before deactivation occurs, with DME becoming the main product. Importantly, improved olefin selectivities are also observed for this sample. C2-C3 olefin selectivities increase gradually with increasing TOS when conversion is near 100% and reach maximum selectivities of 29.7% and 35.9%, respectively, at complete conversion, and approaches olefin selectivities for SAPO-34 (FIG. 19F). Upon regeneration of the spent catalyst, similar olefin selectivities are observed with only a slight decrease in catalyst lifetime (FIGS. 24 and 25, below).

Figure 19A:
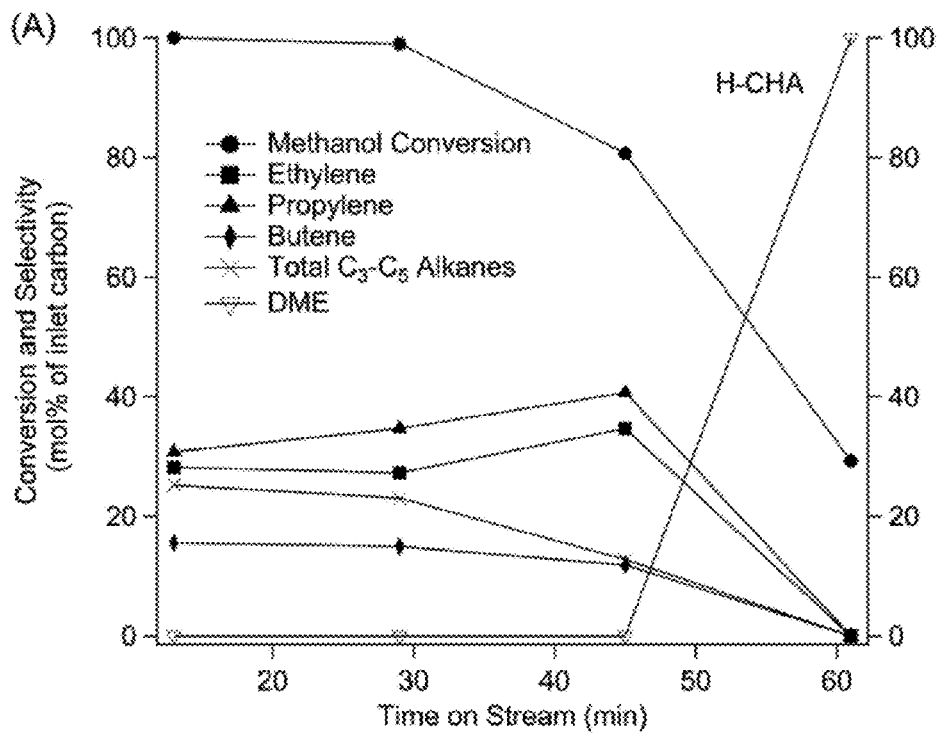
Figure 19B:
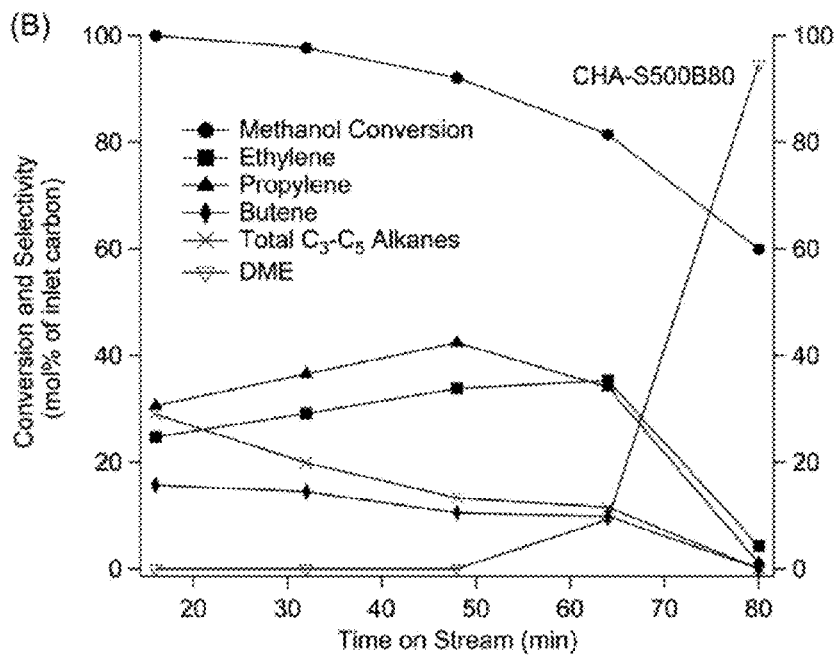
Figure 19C:
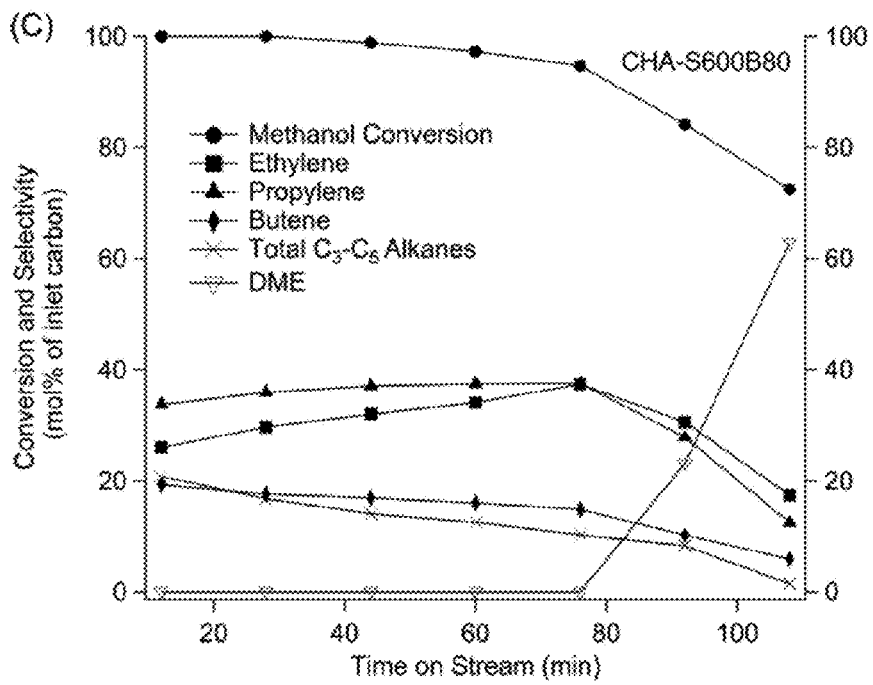
Figure 19D:
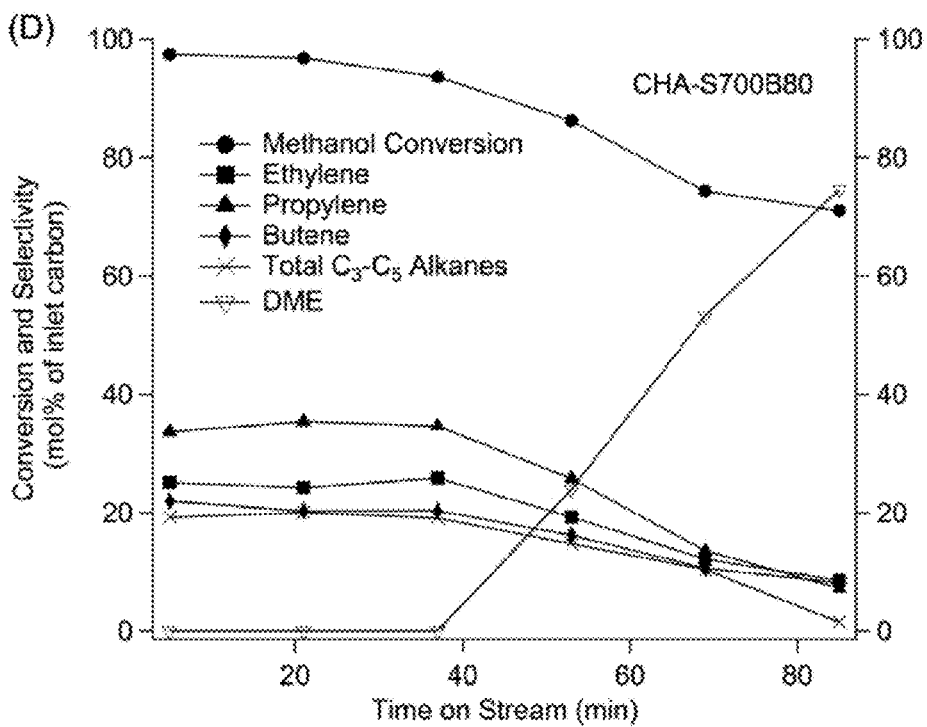
Figure 19E:
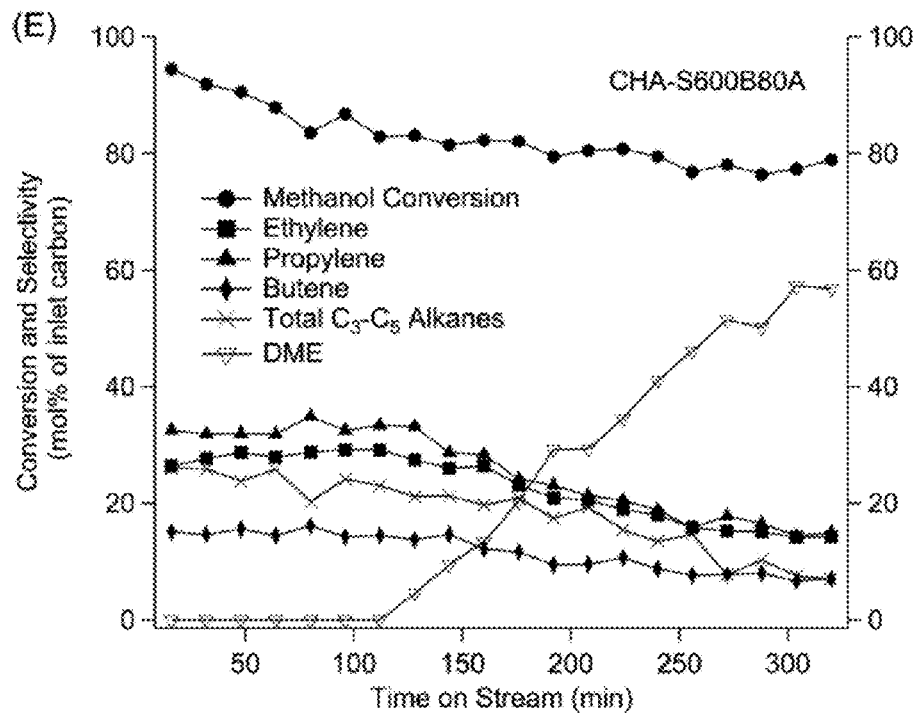
Figure 19F:
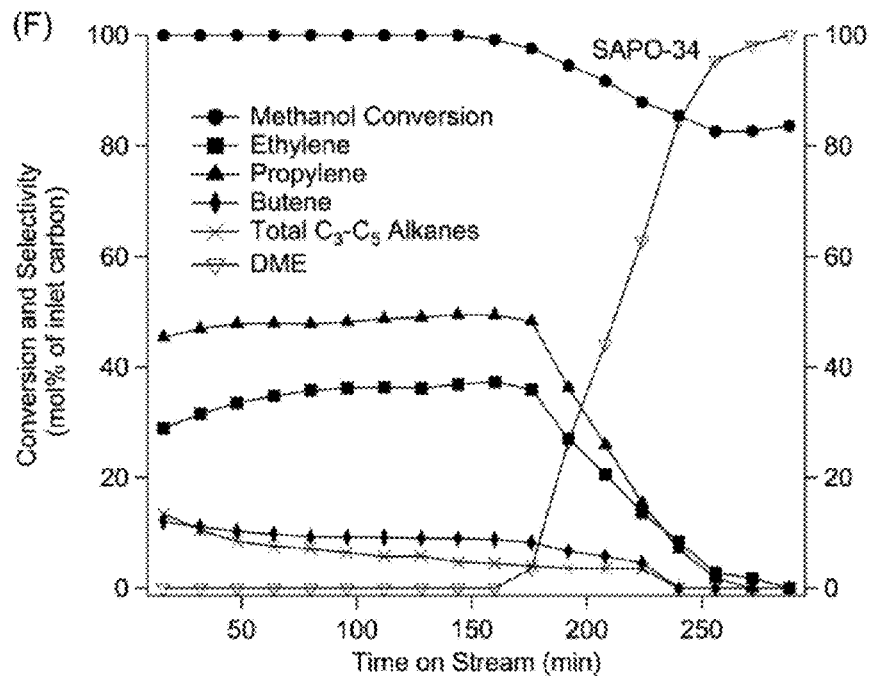
Figure 20A:
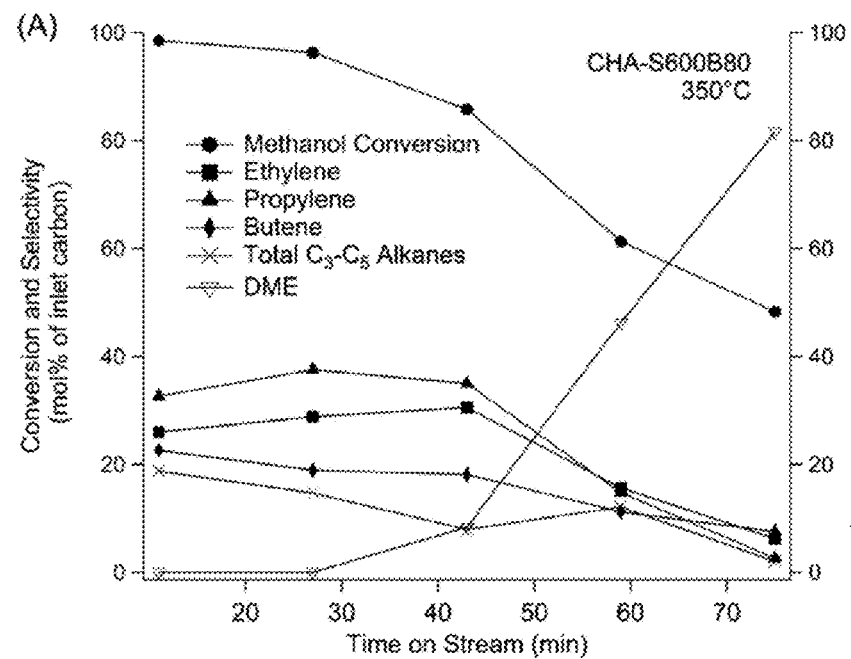
FIGS. 20A-D show representative MTO reaction data for 600° C.-steamed CHA (CHA-S600B80) obtained at reaction temperatures of 350° C.
Figure 20B:
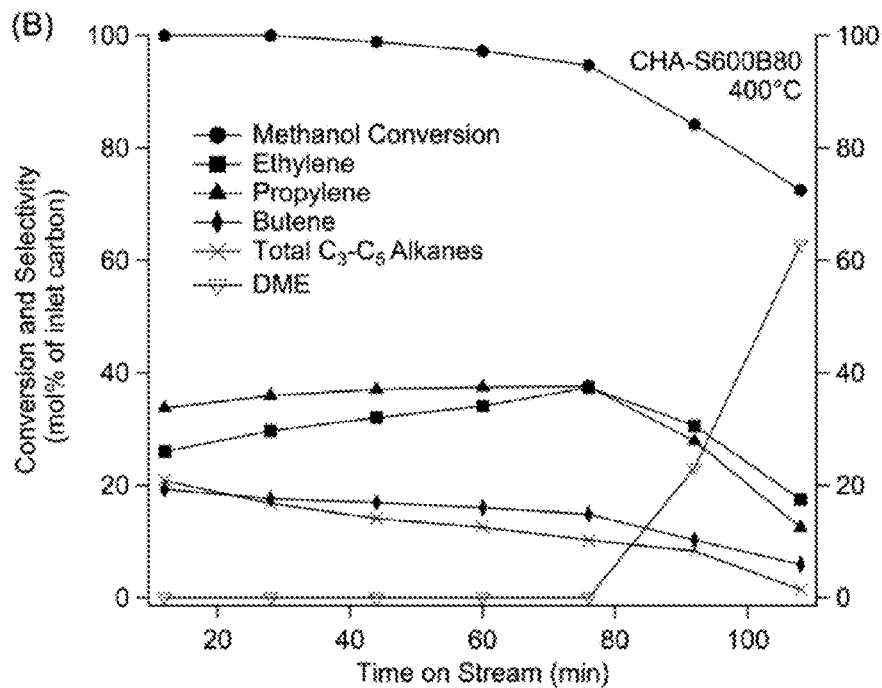
Figure 20C:
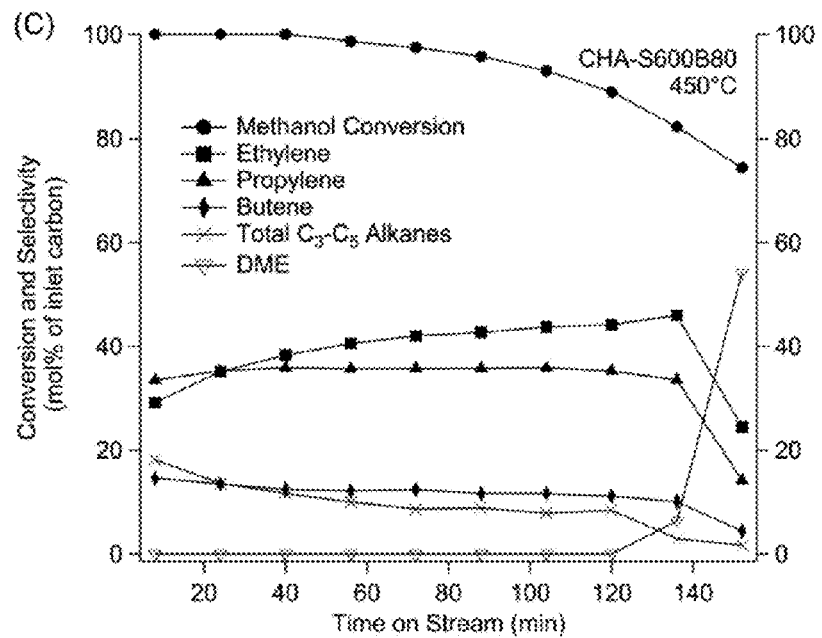
Figure 20D:
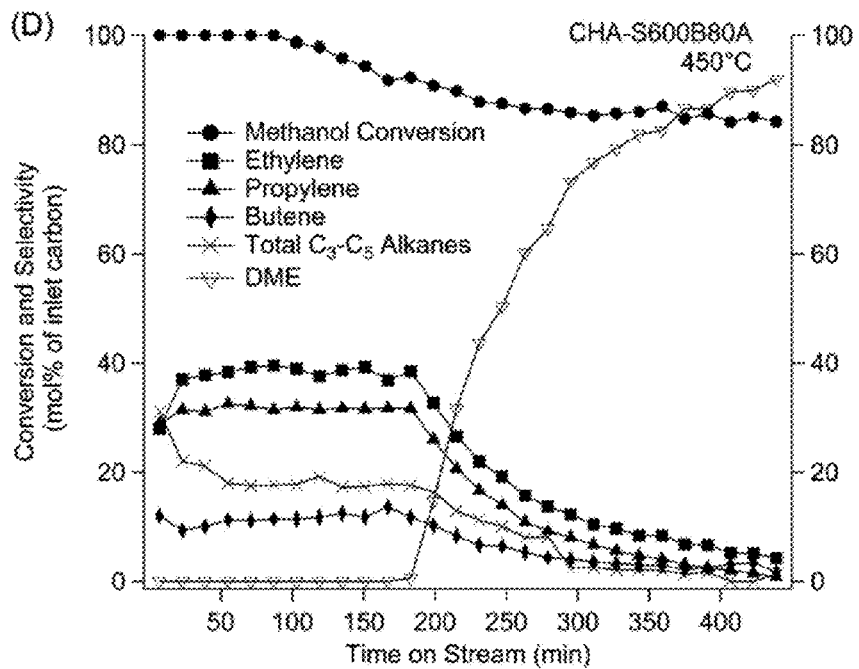

The lifetime of the 600° C.-steamed CHA is improved further after acid washing (FIG. 19E). Methanol conversion decreases slowly and remains steady around 80% until approximately 240 min (5.0 g-MeOH/g-cat) TOS. The combined ethylene and propylene selectivity remains steady at approximately 61% for 100 min TOS before gradually declining.

Increasing the steaming temperature further to 700° C. gives poorer MTO activity compared to CHA-S600B80, likely due to the increased severity of steaming at 700° C. Ethylene and propylene reach selectivities of 24.3% and 35.4%, respectively, at 96.8% methanol conversion (21 min TOS). Conversion drops below 80% by approximately 60 min TOS, giving a reaction profile similar to the 500° C.-steamed CHA.

The improvements in selectivities and catalyst lifetime of the 600° C.-steamed CHA may be attributed to modifications in the acidity of the catalysts resulting from the extraction of framework aluminum. It is also likely that the mesoporosity created by steaming plays a role in the extended lifetimes. It has been observed that the introduction of mesopores in microporous zeolite catalysts facilitates mass transport to the micropores and leads to longer catalyst lifetimes. This trend has been reported by Wu et al., *J. Catal.*, 2013, 298, 27-40 who evaluated hierarchical SSZ-13 that was synthesized using the N,N,N-trimethyl-adamantyl ammonium OSDA in combination with a mesoporogen. These introduced mesopores result in improved lifetimes for the MTO reaction by allowing greater utilization of the micropore volume. As demonstrated by the $NH_3$ and isopropylamine TPD data, the 600° C.-steamed CHA sample appears to have the best balance of intact Brønsted acid sites and access to those sites via the mesoporosity introduced by the steaming process that could account for the excellent reaction behavior observed.

Example 2.5.2. Effect of Reaction Temperature

The effects of reaction temperature on the activity of CHA-S600B80 and CHA-S600B80A are illustrated in FIG. 20. The most apparent trend in the reaction profiles for CHA-S600B80 when the reaction temperature was increased from 350 to 450° C. is the increase in catalyst lifetime. At 350° C., methanol conversion is initially near 100% but declined below 80% after approximately 59 min (1.3 g-MeOH/g-cat) of TOS, while at 400° C., the lifetime was 108 min (2.3 g-MeOH/g-cat). Increasing the reaction temperature further to 450° C. resulted in the longest lifetime at 152 min (3.2 g-MeOH/g-cat). Further, the maximum combined ethylene and propylene selectivity increased at 450° C. to 74.2% at 100% conversion, approaching olefin selectivities observed for SAPO-34 (FIG. 19F).

Figure 22A:
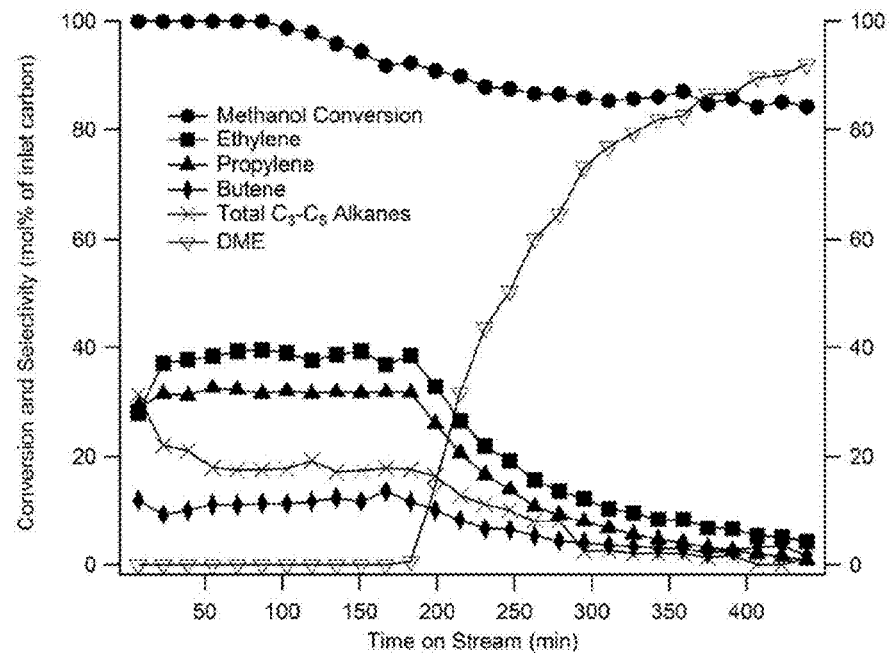
FIGS. 22A-B shows time-on-stream reaction profiles obtained at 450° C. for fresh 600° C. steamed and acid washed CHA (FIG. 22A) and regenerated catalyst (FIG. 22B).
Figure 22B:
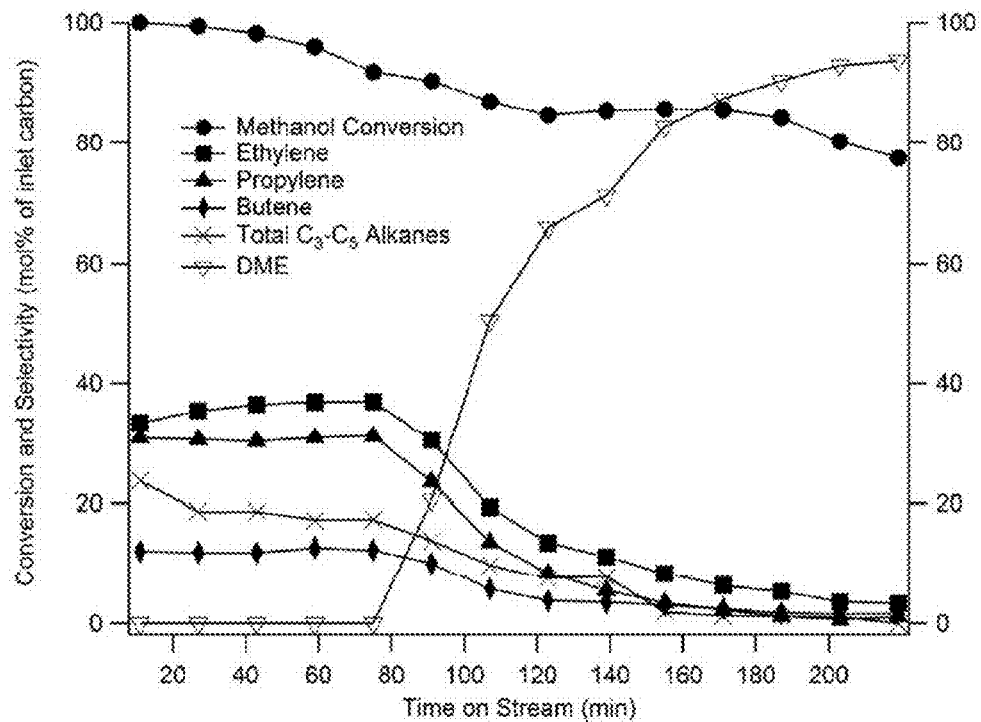

Similarly, the acid-washed sample shows increased in lifetime and olefin selectivities at 450° C. CHA-S600B80A converted methanol to ethylene and propylene steadily at an average of 69% combined selectivity for almost 200 min (4.1 g-MeOH/g cat) TOS before DME became the main product. Further, ethylene selectivities increased for both CHA-S600B80 and CHA-S600B80A when the reaction temperature was increased from 400 to 450° C. so that more ethylene than propylene was produced at 450° C. Regeneration of CHA-S600B80A at 450° C. resulted in some loss in olefin selectivities and lifetime (FIGS. 22A-B).

Figure 21A:
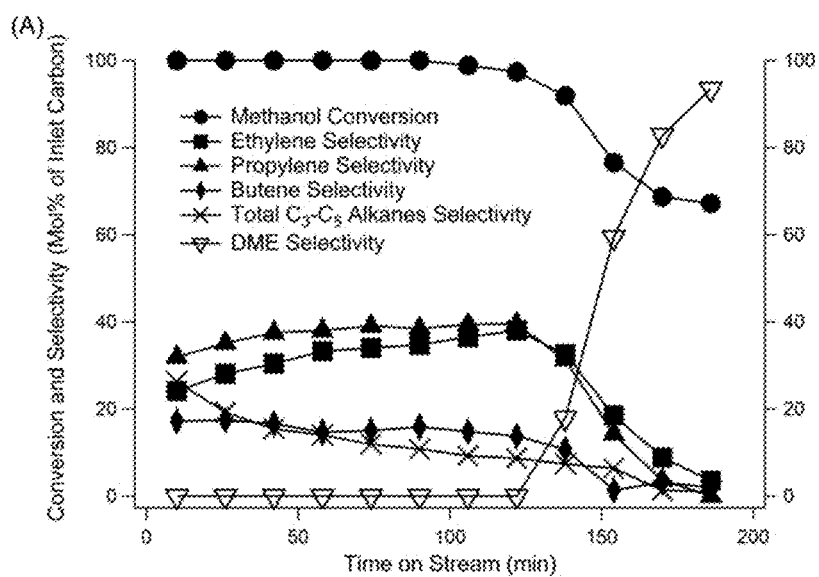
FIGS. 21A-B shows time-on-stream reaction profiles obtained at 400° C. for fresh 600° C. steamed CHA (FIG. 21A) and regenerated catalyst (FIG. 21B).
Figure 21B:
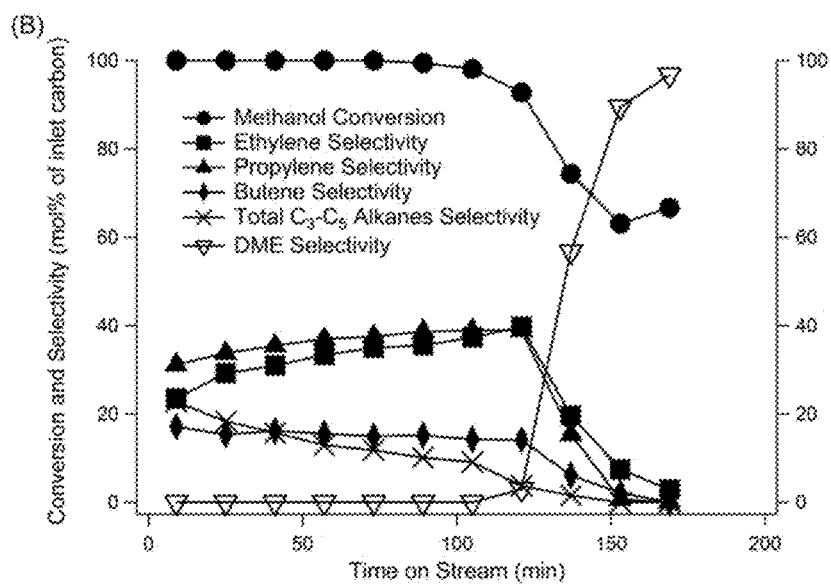

An additional batch of steamed CHA was prepared to determine whether the activity could be recovered by regeneration. CHA was steamed for 8 h at 600° C. under a steam partial pressure of 47.3 kPa, and a portion of the steamed material was acid washed in the same manner as described in the Experimental section. Reaction testing was conducted using a 10% methanol/inert feed at a WHSV of 1.3 h−1. The reaction profiles at 400° C. of the fresh and regenerated 600° C. steamed CHA are shown in FIGS. 21A-B, respectively. The activity of the 600° C. steamed and acid washed CHA was evaluated over two reaction cycles at 450° C. and the reaction profiles are shown in FIGS. 22A-B.

FIGS. 20A-D shows the reaction profiles of the 600° C. steamed CHA obtained at reaction temperatures of 350° C. and 450° C. and the steamed and acid washed CHA obtained at a reaction temperature of 450° C. These data show that increasing the reaction temperature to 450° C. further improved the olefin selectivities and lifetime.

Example 2.6. Regeneration of CHA Catalysts

FIGS. 21A-B and 22A-B shows a comparison of the MTO reaction profiles for a fresh 600° C. steamed CHA and the regenerated catalyst. The regenerated catalyst achieved olefin selectivities very similar to the fresh catalyst and only a small loss in lifetime (approximately 140 min. vs 150 min TOS), suggesting that the steamed CHA catalyst was able to retain MTO activity after at least one reaction cycle. Regeneration of the 600° C. steamed and acid washed CHA resulted in a greater loss in lifetime.

Example 3. Zeolite RHO

Example 3.1. Synthesis

Zeolite Rho was prepared according to the method described U.S. Pat. No. 3,904,738. A synthesis gel was prepared with molar composition 0.3 $Na_2O$:0.1 $Al_2O_3$:1 $SiO_2$:0.04 $Cs_2O$:8 $H_2O$ using Catapal B as the alumina source, Ludox HS-40 as the silica source, Mallinckrodt NaOH pellets as the NaOH source, and Aldrich 50 wt. % CsOH aqueous solution as the Cs source. In a typical synthesis, the alumina source was added to a solution containing NaOH and water. The mixture was heated at 110° C. until the alumina was dissolved, forming a clear solution. The CsOH was then added to the solution followed by the silica source. The reaction mixture was covered and stirred for 72 h at room temperature and then transferred to a Teflon-lined autoclave and heated for 1-3 days at 100° C. The crystallized product was recovered by centrifugation, washed with water followed by acetone and dried overnight at 100° C. The $NH_4^+$ form of the product was obtained in the same manner as that described for CHA.

TABLE 5

Summary of RHO dealumination treatments

| Framework Type | Sample Name | Steaming Conditions |
|---|---|---|
| RHO | $NH_4$—RHO | NA |
| | RHO-S600B80 | 8 h at 500° C. |
| | RHO-S700B80 | 8 h at 600° C. |
| | RHO-S800B80 | 8 h at 700° C. |

Example 3.2. Observations

The powder XRD patterns of the as-synthesized and steamed RHO are shown in FIG. 23, which indicate that some crystallinity was lost during the steam treatments. Under the steaming conditions tested, zeolite RHO appeared stable up to 800° C. Similarly, the $^{27}Al$ NMR spectrum of the as-synthesized RHO (FIG. 24(A)) showed that all aluminum was initially incorporated in the framework, while the steamed RHO (FIG. 24(B)) contained both framework and extra framework aluminum species.

Figure 26:
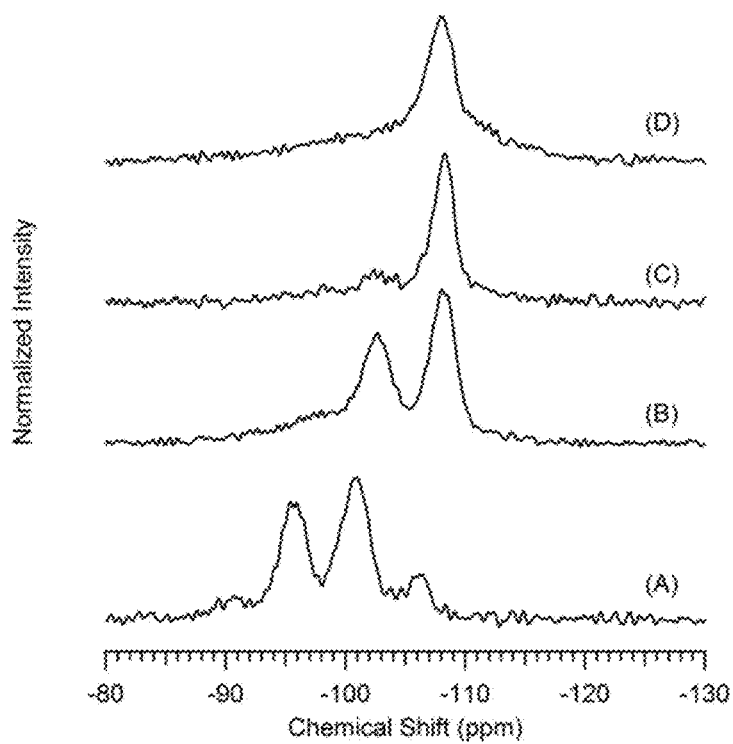
FIG. 26 shows $^{29}Si$ NMR of A) as-synthesized RHO ($NH_4^+$ form), B) 600° C. steamed, C) 700° C. steamed, and D) 800° C. steamed RHO.
Figure 27A:
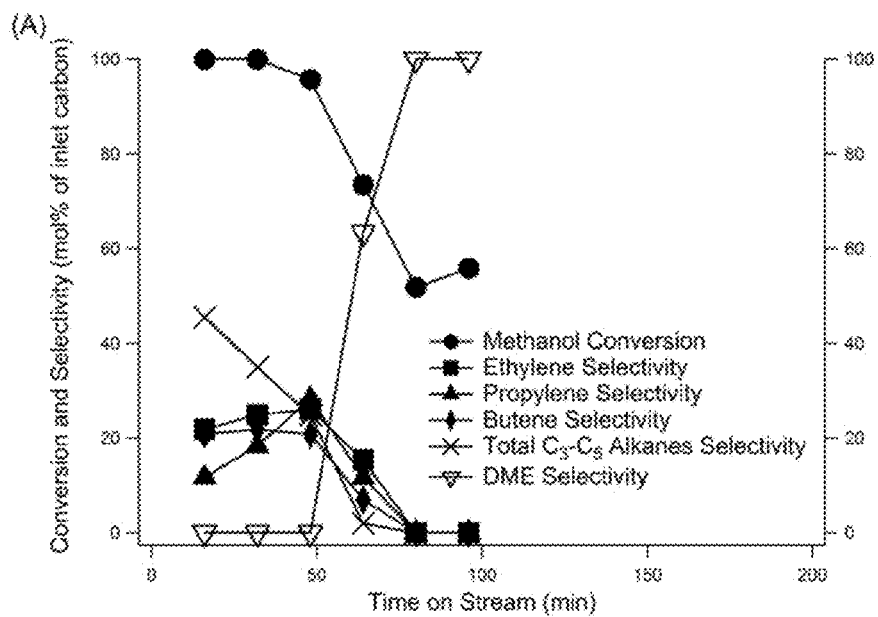
Figure 27B:
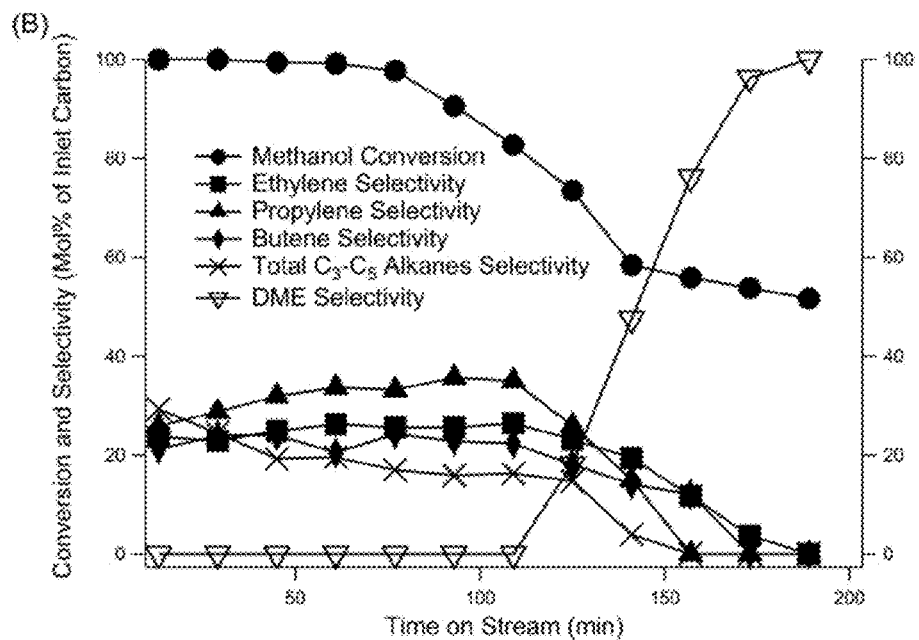
Figure 27C:
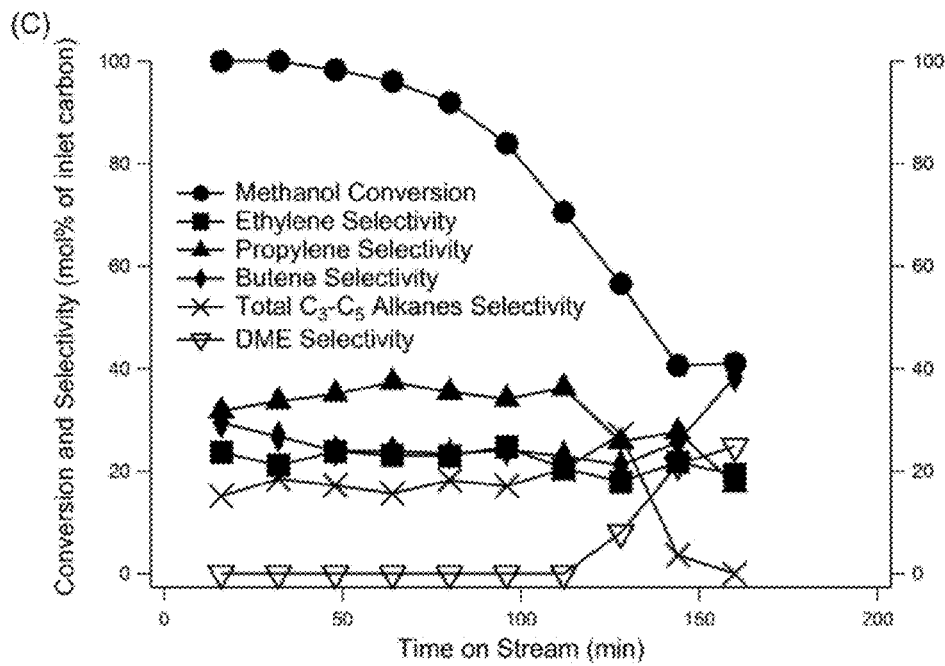
Figure 27D:
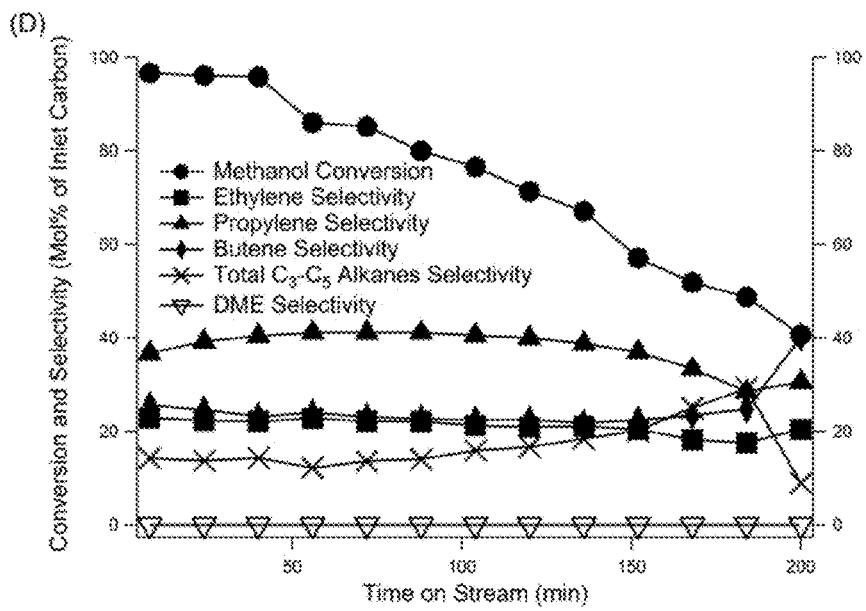
Figure 27E:
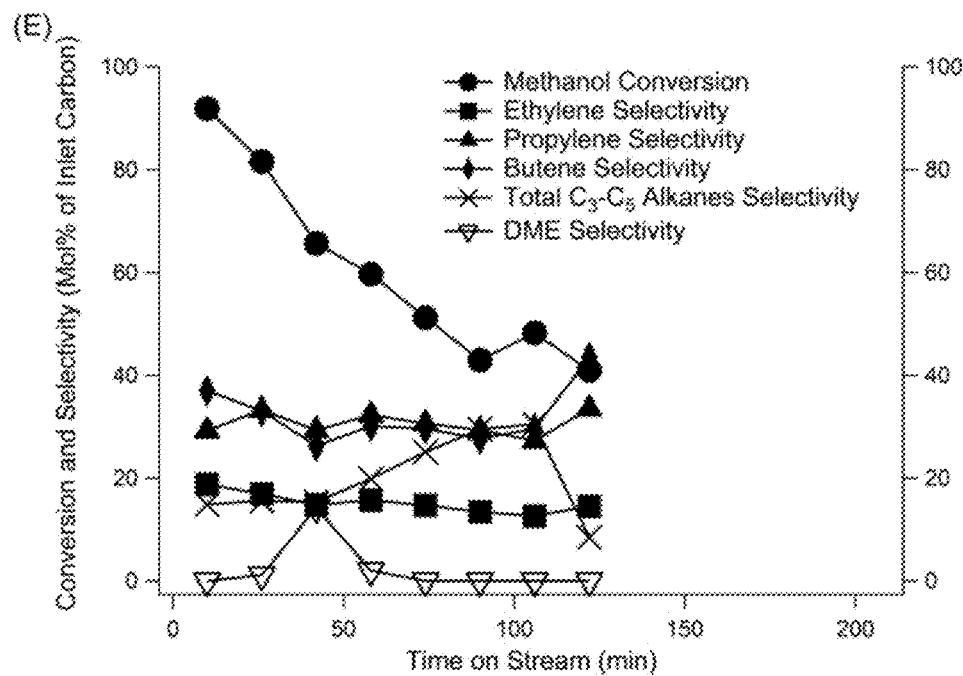
Figure 27F:
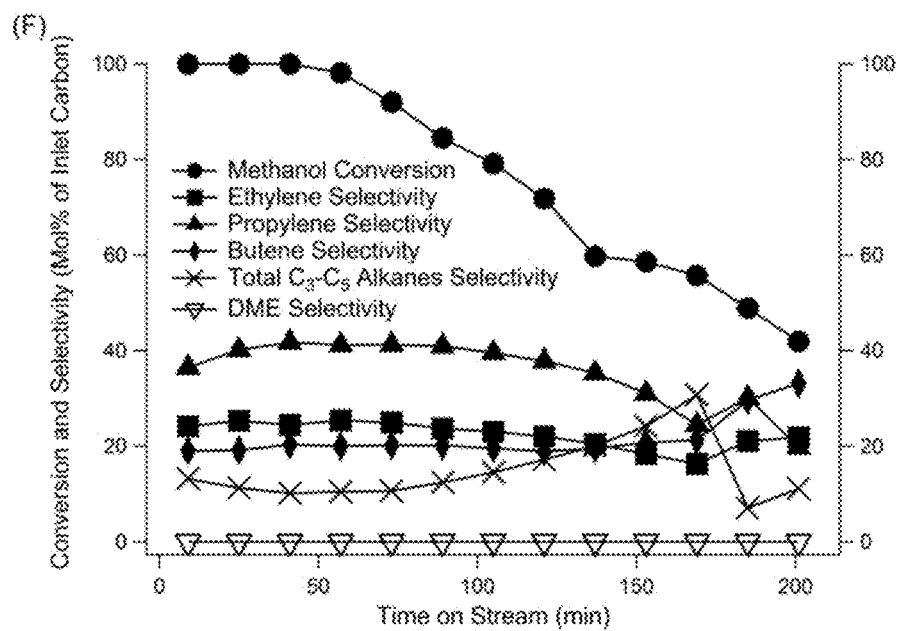

Conversion of tetrahedral, framework aluminum to higher-coordinated aluminum during the steam treatments was observed in the $^{27}Al$ NMR spectra (FIG. 25), which indicated the presence of penta-coordinated (~30 ppm) and octahedral (hexacoordinate) (~0 ppm) aluminum species in the steamed samples. FIG. 26 shows the $^{29}Si$ NMRs of the as-synthesized and steamed RHO samples, respectively. The $^{29}Si$ NMR spectra show that the amount of aluminum in the second coordination spheres of the framework silicon decreased after the steam treatments and is consistent with the $^{27}Al$ NMR in suggesting that aluminum was extracted from the framework.

Example 3.3. MTO Reactivity

Table 5 provides a summary of the MTO reactivity data for the dealuminated RHO zeolites. FIGS. 27A-F show MTO reaction data for the as-synthesized and steamed RHO samples. The unsteamed $NH_4$—RHO (FIG. 27A) deactivated rapidly after approximately 60 min TOS and reached a maximum combined ethylene and propylene selectivity of 43.3% at 100% conversion. In comparison, the steamed RHO samples showed improved lifetimes and olefin selectivities. At a reaction temperature of 400° C., methanol conversions remained above 80% for more than 90 min TOS for all of the steamed RHO samples. At 400° C., the highest combined ethylene and propylene selectivity (59.6%) was obtained by RHO steamed at 800° C., and the selectivity increased to 66.2% when the reaction temperature was raised to 450° C.

Example 4. Zeolite ZK-5(KFI)

Example 4.1. Synthesis

Zeolite ZK-5 (KFI) was synthesized following the method described in U.S. Pat. No. 3,720,753. A synthesis gel was prepared with molar composition 0.24 $K_2O$:0.167 $Al_2O_3$:1 $SiO_2$:0.030 $Cs_2O$:7.5 $H_2O$ using Macron KOH pellets as the KOH source, JT Baker $Al(OH)_3$ as the aluminum source, Ludox LS-30 colloidal silica as the silica source and Aldrich $CsOH*H_2O$ powder as the CsOH source. In a typical synthesis, the aluminum source was added to a solution of KOH and CsOH in water. The aluminum was dissolved by heating the mixture at 110° C. until a clear solution formed. The silica source was then added to the solution. The gel was stirred until homogenous, transferred to a Teflon-lined autoclave and heated at 100° C. for 4.5 days. The product (Si/Al=3.1) was recovered by centrifugation, washed extensively with water followed by acetone, and dried overnight at 100° C. The $NH_4^+$ form of the as-synthesized KFI zeolite was obtained by three ion exchanges in 1 M $NH_4NO_3$ (100 mL solution per gram solid) at 90° C. for 2 h.

Example 4.1. Steaming Treatments

Steaming was conducted in a horizontal tube furnace with a water saturator upstream of the sample. Zero grade air was bubbled at 50 cc/min through the water saturator, which was held at 80° C. $NH_4^+$ exchanged zeolite was loaded in ceramic calcination boats and placed in the center of the furnace, which was then heated at 1° C./min to the desired steaming temperature (500° C., 600° C., or 700° C.) and held at that temperature for 8 h. The entire process was carried out under flowing water vapor and air mixture.

Example 4.2. MTO Reaction Testing

Catalysts for reaction testing were crushed and sieved to obtain particles between 0.6 mm and 0.18 mm. Approximately 200 mg of the sieved catalyst was supported between glass wool beds in a continuous flow reactor. Prior to reaction, all samples were calcined in-situ under a flow of medical-grade air, during which the temperature was ramped at 1° C./min to 150° C., held for 3 hours, then ramped at 1° C./min to 580° C. and held for 12 hours. The reaction was then conducted at 350, 400, or 450° C. with a feed of 10% methanol in inert pumped at a WHSV of 1.3 $h^{-1}$.

TABLE 6

Summary of KFI dealumination treatments

| Framework Type | Sample Name | Steaming Conditions |
|---|---|---|
| KFI | NH$_4$—KFI | NA |
| | KFI-S600B80 | 8 h at 600° C. |
| | KFI-S700B80 | 8 h at 700° C. |
| | KFI-S800B80 | 8 h at 800° C. |

Example 4.3. Characterization and Results

The powder XRD patterns of the as-synthesized and steamed KFI samples are shown in FIG. 28, which indicate that some crystallinity was lost during the steam treatments. Under the steaming conditions tested, zeolite KFI was stable up to 700° C.

Figure 29:
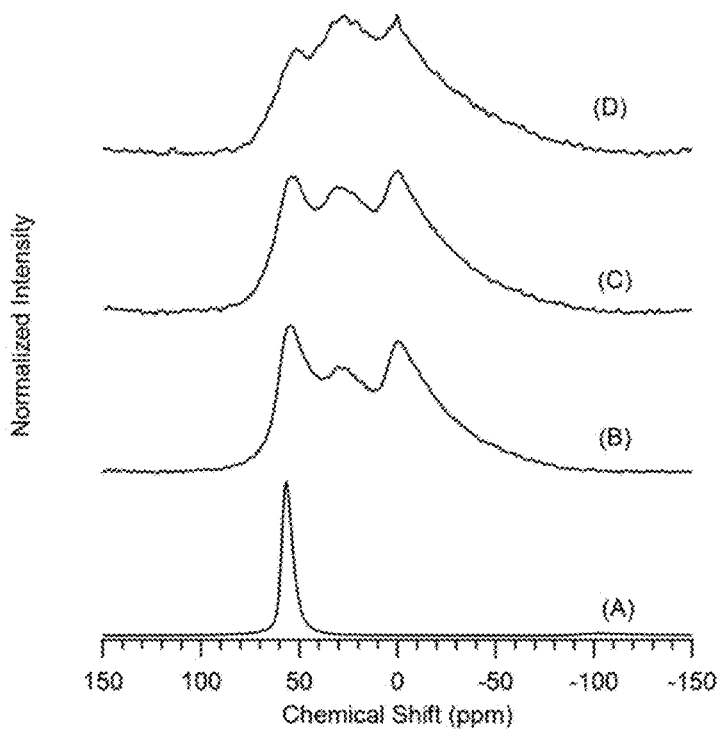
FIG. 29 shows $^{27}Al$ NMR spectra of A) as-synthesized KFI ($NH_4^+$ form), B) 600° C. steamed, C) 700° C. steamed, and D) 800° C. steamed KFI
Figure 30:
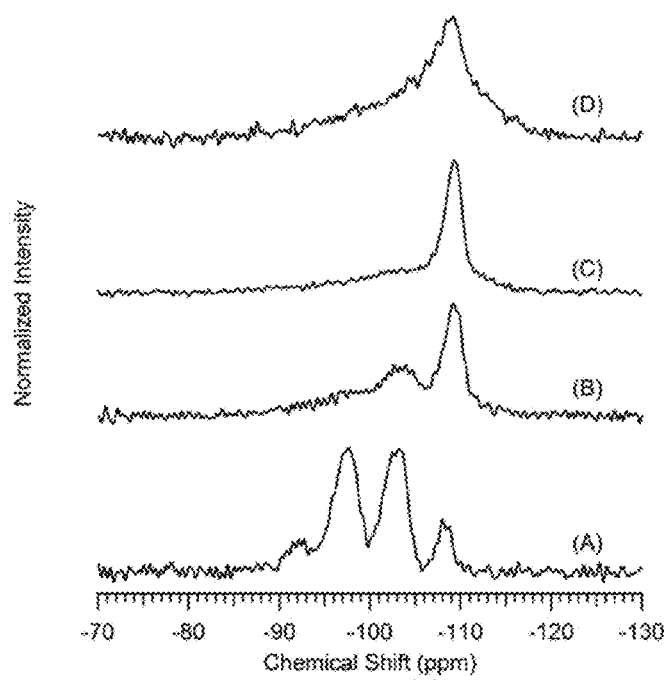
FIG. 30 shows $^{29}Si$ NMR of A) as-synthesized KFI ($NH_4^+$ form), B) 600° C. steamed, C) 700° C. steamed, and D) 800° C. steamed KFI.

Conversion of tetrahedral, framework aluminum to higher-coordinated aluminum during the steam treatments was observed in the $^{27}$Al NMR spectra (FIG. 29), which indicated the presence of penta-coordinated (~30 ppm) and octahedral (~0 ppm) aluminum species in the steamed samples. FIG. 30 shows the $^{29}$Si NMRs of the as-synthesized and steamed KFI samples. The $^{29}$Si NMR spectra show that the amount of aluminum in the second coordination spheres of the framework silicon decreased after the steam treatments and was consistent with the $^{27}$Al NMR in suggesting that aluminum is extracted from the framework.

MTO Reactivity

Figure 31A:
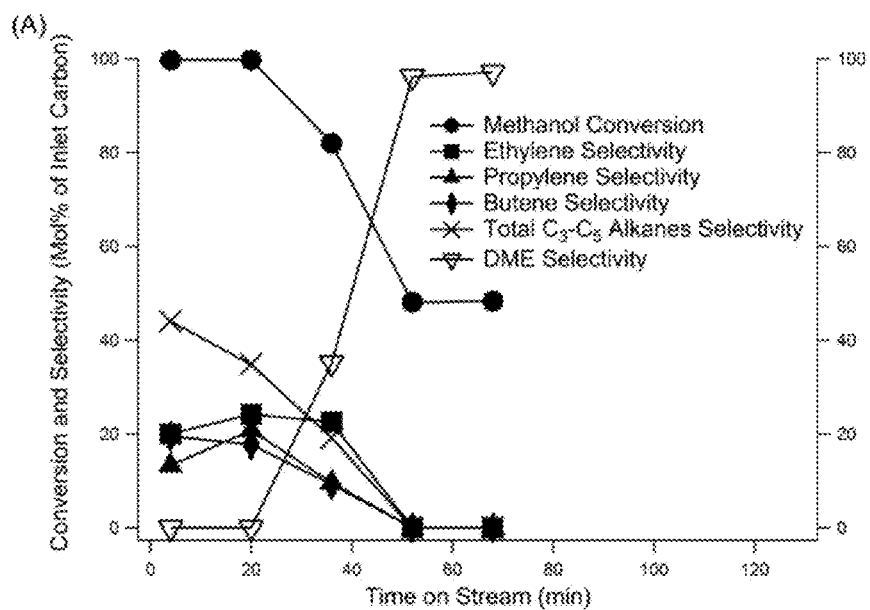
FIGS. 31A-C shows time-on-stream reaction profiles obtained at 400° C. for as-synthesized $NH_4$—KFI (FIG. 31A); 600° C. steamed KFI (FIG. 31B); and 700° C. steamed KFI (FIG. 31C).
Figure 31B:
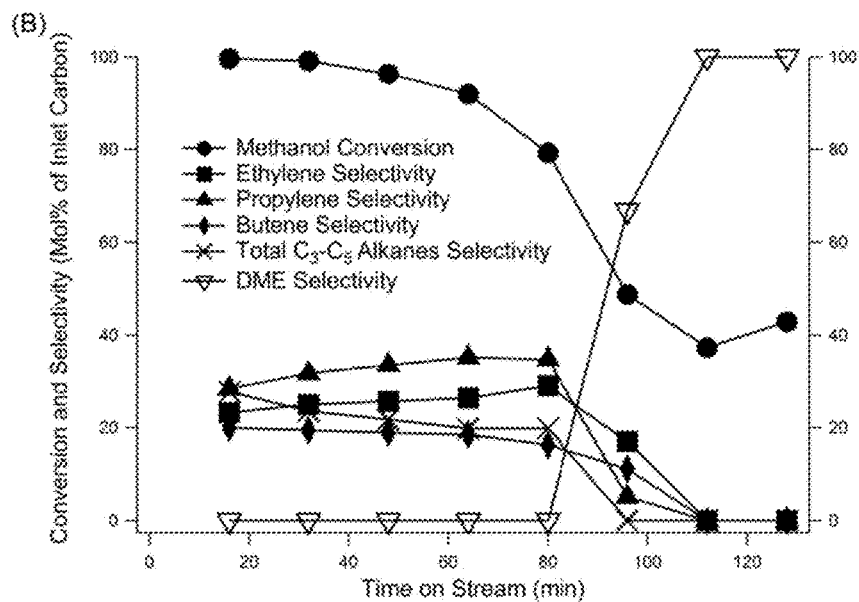
Figure 31C:
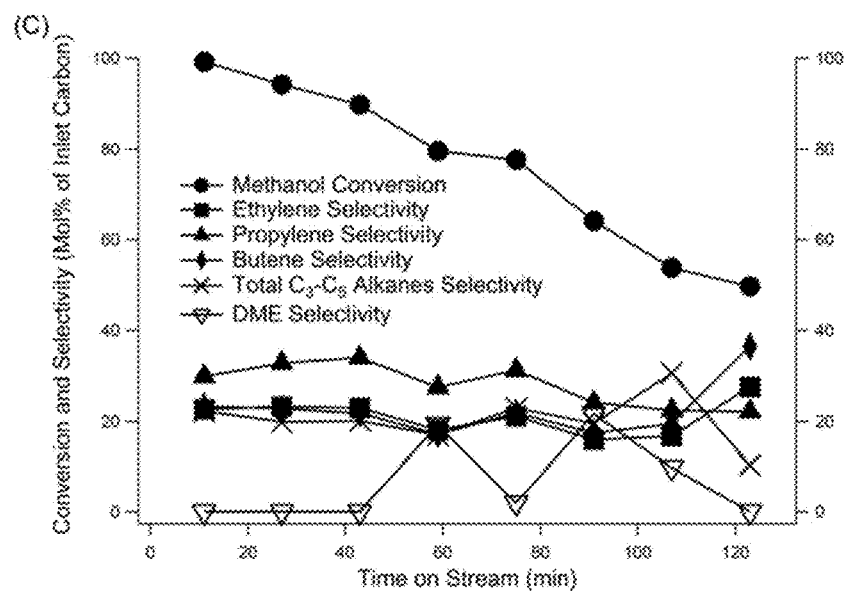

Table 2 provides a summary of the MTO reactivity data for the dealuminated zeolites. FIG. 31A-C show MTO reaction data for the as-synthesized and steamed KFI samples. Reaction data for KFI show a similar (to RHO) increase in lifetime and olefin selectivities after steam treatment. The maximum combined ethylene and propylene selectivity increased from 44.7% for the unsteamed NH$_4$—KFI to 52.6% for the 700° C. steamed KFI.

TABLE 7

Summary of MTO reactivity for dealuminated zeolite catalysts

| Framework Type | Sample | Reaction Temperature | Maximum Methanol Conversion | Maximum Combined C$_2$—C$_3$ Olefin Selectivity at Maximum Conversion | Time to Deactivation $^a$ (g-MeOH/g-cat) |
|---|---|---|---|---|---|
| RHO | NH$_4$—RHO | 400° C. | 100% | 43.3% | 1.3 |
| | 600° C. Steamed RHO | 400° C. | 100% | 51.6% | 2.6 |
| | 700° C. Steamed RHO | 400° C. | 100% | 54.8% | 2.3 |
| | 800° C. Steamed RHO | 400° C. | 96.6% | 59.6% | 2.2 |
| | 800° C. Steamed RHO | 350° C. | 91.9% | 48.0% | 0.87 |
| | 800° C. Steamed RHO | 450° C. | 100% | 66.2% | 2.2 |
| KFI | NH$_4$—KFI | 400° C. | 99.7% | 44.7% | 1.0 |
| | 600° C. Steamed KFI | 400° C. | 99.6% | 51.6% | 1.7 |
| | 700° C. Steamed KFI | 400° C. | 99.3% | 52.6% | 1.5 |
| CHA | 600° C. Steamed CHA | 350° C. | 98.6% | 58.6% | 0.23 |
| | 600° C. Steamed CHA | 400° C. | 100% | 73.2% | 3.3 |
| | 600° C. Steamed CHA Regenerated | 400° C. | 100% | 74.2% | 2.9 |
| | 600° C. Steamed CHA | 450° C. | 100% | 74.2% | 3.2 |
| | 600° C. Steamed and Acid Washed CHA | 450° C. | 100% | 71.4% | >9.0 |
| | 600° C. Steamed and Acid Washed CHA Regenerated | 450° C. | 100% | 64.2% | 4.5 |

$^a$ First time point where conversion drops below 80%

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes The following references may be useful in understanding the background and certain aspects of the present invention:
1. Olsbye, U.; Svelle, S.; Bjorgen, M.; Beato, P.; Janssens, T. V. W.; Joensen, F.; Bordiga, S.; Lillerud, K. P. *Angew. Chem. Int. Ed.* 2012, 51, 5810.
2. Froment, G. F.; Dehertog, W. J. H.; Marchi, A. J. In *Catalysis: Volume 9*, Spivey, J. J., Ed. The Royal Society of Chemistry: 1992; Vol. 9, pp 1.
3. Zones, S. I., Zeolite SSZ-13 and its method of preparation. U.S. Pat. No. 4,544,538 A, 1985.
4. Bleken, F.; Bjørgen, M.; Palumbo, L.; Bordiga, S.; Svelle, S.; Lillerud, K.-P.; Olsbye, U. *Top. Catal.* 2009, 52, 218.
5. Yuen, L.-T.; Zones, S. I.; Harris, T. V.; Gallegos, E. J.; Auroux, A. *Microporous Mater.* 1994, 2, 105.
6. Cartlidge, S.; Patel, R. In *Zeolites: Facts, Figures*, Future, Jacobs, P. A.; vanSanten, R. A., Eds. Elsevier: Amsterdam, 1989; pp 1151.
7. Bourgogne, M.; Guth, J. L.; Wey, R., Process for the preparation of synthetic zeolites, and zeolites obtained by said process. U.S. Pat. No. 4,503,024 A, 1985.
8. Robson, H. E., Zeolite RHO. U.S. Pat. No. 3,904,738 A, 1987.

What is claimed:

1. A method for improving the catalytic activity of a precursor 8-MR zeolite, the method comprising:
   (a) treating the precursor 8-MR zeolite, prepared in the absence of any organic structure directing agent and having an Si/Al atom ratio of less than 5, with high temperature steam for a period of time sufficient to extract at least a portion of the aluminum oxide from the precursor zeolite framework to form a steam-treated zeolite of the same topology as the precursor zeolite, and
   (b) optionally washing the steam-treated zeolite with acid to remove the extracted aluminum oxide;
   wherein:
   the steam has a temperature in a range of from 350° C. to 650° C.;
   the precursor 8-MR zeolite contains aluminum that is practically all tetrahedral, as measured by $^{27}$Al NMR;
   the precursor 8-MR zeolite has a framework comprising 8-MR as the largest ring for entrance of molecules into the intracrystalline void space, and
   the ratio of the silicon to tetrahedral aluminum atoms in the steam-treated zeolite is in a range of from 5 to 120.

2. The method of claim 1, wherein the ratio of the silicon to tetrahedral aluminum atoms in the steam-treated zeolite is in a range of from 10 to 20.

3. The method of claim 1, wherein the precursor 8-MR ring zeolite has a CHA, RHO, or KFI framework.

4. The method of claim 1, wherein the high temperature of the steam is in a range of from 500° C. to 600° C.

5. The method of claim 1, wherein Si/Al atom ratio of the precursor zeolite is in a range of from 2.5 to less than 5.

6. The method of claim 1, further comprising exchanging any alkali or alkaline earth metals in the precursor 8-MR zeolite with an acidifying agent prior to exposing the precursor 8-MR zeolite to the high temperature steam.

7. The method of claim 1, wherein at least a portion of the aluminum sites in the precursor 8-MR zeolite are acid in character.

8. The method of claim 1, wherein the steam-treated zeolite contains tetrahedral, pentacoordinate and hexacoordinate aluminum, as characterized by $^{27}$Al NMR.

9. The method of claim 1, wherein the atomic ratio of tetrahedral aluminum to total aluminum content in the steam-treated zeolite is in a range of from about 0.12 to about 0.6.

10. The method of claim 1, wherein the steam-treated zeolite has a micropore volume in a range of from 0.03 to 0.8 cc/gram of the steamed zeolite.

11. The method of claim 1, wherein the steam-treated zeolite has Brønsted acid site density in a range of from 0.6 to 1.2 mmol/gram of the steamed zeolite, as determined by ammonia temperature-programmed desorption.

12. The method of claim 8, further comprising washing the steam-treated zeolite with acid.

13. The method of claim 12, wherein the acid wash removes at least a portion of pentacoordinate, hexacoordinate aluminum, or both pentacoordinate and hexacoordinate aluminum formed in the steam-treated zeolite.

14. The method of claim 1, wherein the precursor 8-MR zeolite and the steam treated 8-MR zeolite have ABW, ANA, BIK, BRE, CAS, CHA, EAB, EDI, EPI, ERI, ESV, GIS, GOO, JBW, KFI, LEV, LTA, MER, MON, PAU, PHI, RHO, THO, TSC, UFI, or YUG topologies.

15. The method of claim 1, wherein the high temperature steam contains water in a range of from about 20 vol % to about 70 vol % water.

16. The method of claim 1, wherein the steam-treated 8-MR zeolite exhibits a $^{29}$Si-MAS NMR spectrum containing no measurable Si(3Al) environment.

17. The method of claim 3, wherein the high temperature of the steam is in a range of from 500° C. to 600° C.

18. The method of claim 3, wherein the high temperature steam contains water in a range of from about 20 vol % to about 70 vol % water.

19. The method of claim 3, further comprising exchanging any alkali or alkaline earth metals in the precursor 8-MR zeolite with an acidifying agent prior to exposing the precursor 8-MR zeolite to the high temperature steam.

20. The method of claim 3, wherein the steam-treated zeolite contains tetrahedral, pentacoordinate, and hexacoordinate aluminum, as characterized by $^{27}$Al NMR.

21. The method of claim 3, wherein the atomic ratio of tetrahedral aluminum to total aluminum content in the steam-treated zeolite is in a range of from about 0.12 to about 0.6.

22. The method of claim 3, wherein the ratio of the silicon to tetrahedral aluminum atoms in the steam-treated zeolite is in a range of from 10 to 20.

23. The method of claim 3, wherein the steam-treated zeolite has a micropore volume in a range of from 0.03 to 0.8 cc/gram of the steamed zeolite.

24. The method of claim 3, wherein the steam-treated zeolite has Brønsted acid site density in a range of from 0.6 to 1.2 mmol/gram of the steamed zeolite, as determined by ammonia temperature-programmed desorption.

25. The method of claim 1, wherein the steam-treated 8-MR zeolite exhibits a $^{29}$Si-MAS NMR spectrum containing no measurable signals attributable to Si(3Al) sites.

26. The method of claim 3, further comprising washing the steam-treated zeolite with acid.

27. The method of claim 12, wherein the acid comprises HCl, $H_2SO_4$, $H_3PO_4$, or oxalic acid.

28. The method of claim 25, wherein the acid comprises HCl, $H_2SO_4$, $H_3PO_4$, or oxalic acid.

29. The method of claim 1, wherein:
   the precursor 8-MR zeolite and the steam-treated zeolite both have a CHA topology;
   the precursor 8-MR zeolite is prepared by a gel process in the absence of an organic structure directing agent to form an alkali metal-containing product that is subsequently ion-exchanged with an ammonium salt to form the precursor 8-MR zeolite;
   the steam temperature is in a range of from 500° C. to 600° C., the steam containing 46 vol % to 70 vol % water; and wherein
   the ratio of the silicon to tetrahedral aluminum atoms in the steam-treated zeolite is in a range of from 10 to 20.

* * * * *